United States Patent
Yamamoto et al.

(10) Patent No.: US 9,129,187 B2
(45) Date of Patent: Sep. 8, 2015

(54) IMAGE RECONSTRUCTION METHOD AND DEVICE

(75) Inventors: Mariko Yamamoto, Kokubunji (JP); Shin-ichiro Umemura, Sendai (JP); Takashi Azuma, Fuchu (JP); Kunio Hashiba, Tokyo (JP)

(73) Assignee: HITACHI MEDICAL CORPORATION, Tokyo (JP)

( * ) Notice: Subject to any disclaimer, the term of this patent is extended or adjusted under 35 U.S.C. 154(b) by 70 days.

(21) Appl. No.: 13/811,964

(22) PCT Filed: Jul. 28, 2011

(86) PCT No.: PCT/JP2011/067201
§ 371 (c)(1),
(2), (4) Date: Feb. 7, 2013

(87) PCT Pub. No.: WO2012/029460
PCT Pub. Date: Mar. 8, 2012

(65) Prior Publication Data
US 2013/0148894 A1    Jun. 13, 2013

(30) Foreign Application Priority Data
Aug. 31, 2010    (JP) .................................. 2010-193031

(51) Int. Cl.
*G06K 9/46*    (2006.01)
*G01S 15/89*    (2006.01)
(Continued)

(52) U.S. Cl.
CPC ................ *G06K 9/46* (2013.01); *G01S 7/52036* (2013.01);
(Continued)

(58) Field of Classification Search
CPC .......... A61B 5/0048; A61B 8/00; A61B 8/58;
A61B 18/18; A61B 5/7235; A61B 8/4483;
A61B 8/0875; A61B 5/4585; A61B 5/1032;
G01S 15/8984; G01S 7/52042; G01S 7/52036;
G01S 17/026; G10K 11/346; Y10S 128/916;
G03B 42/06; G06K 9/46; G06K 9/00624;
G06T 11/003; B60R 2021/01541; G01N
29/07; G01N 29/44; G05D 1/0274; A61F
2002/4666

USPC .......... 367/140; 600/437, 438, 449; 382/190,
382/100, 215, 254, 206, 218
See application file for complete search history.

(56) References Cited

U.S. PATENT DOCUMENTS 4,906,940 A * 3/1990 Greene et al. ................. 382/100
4,987,367 A * 1/1991 Ishikawa et al. .............. 324/227
(Continued)

FOREIGN PATENT DOCUMENTS

| JP | 2006-511298 | 4/2006 |
| JP | 2007-152074 | 6/2007 |

(Continued)

OTHER PUBLICATIONS

Cuiping Li et al., Breast Imaging Using Transmission ultrasound: Reconstructing Tissue Parameters of Sound and Attenuation, 2008 International Conference on BioMedical Engineering and Informatics, pp. 708-712.

*Primary Examiner* — Vu Le
*Assistant Examiner* — Aklilu Woldermariam
(74) *Attorney, Agent, or Firm* — Baker Botts L.L.P.

(57) ABSTRACT

An objective is to enable calculation of a distribution of a physical property such as a density inside a measurement object, even when the distribution of the physical property value is non-uniform, within a feasible period of time without causing image deterioration due to phenomena such as refraction and multiple-reflections caused by the non-uniformity. To this end, the physical property value that makes an evaluation quantity be an extremum is outputted, where the evaluation quantity is a liner sum or a product of exponential function of: an equation residual quantity that is a residual being a difference between an operator term and an external force term of an equation of motion; a non-uniformity detection equation residual quantity that is a residual of an equation of detecting the non-uniformity of the physical property value from a matching degree of solutions of the equation of motion under two types of boundary conditions; and a conditional equation residual quantity that is a residual of a constraint condition.

12 Claims, 16 Drawing Sheets

(51) Int. Cl.
 *G06T 11/00* (2006.01)
 *G01S 7/52* (2006.01)

(52) U.S. Cl.
 CPC ........... *G01S 15/895* (2013.01); *G01S 15/8913* (2013.01); *G01S 15/8927* (2013.01); *G06T 11/006* (2013.01); *G01S 15/8922* (2013.01)

(56) References Cited

U.S. PATENT DOCUMENTS

| | | | |
|---|---|---|---|
| 5,614,670 A * | 3/1997 | Nazarian et al. | 73/146 |
| 6,298,726 B1 * | 10/2001 | Adachi et al. | 73/632 |
| 6,450,036 B1 * | 9/2002 | Ashida et al. | 73/584 |
| 6,491,635 B1 * | 12/2002 | Mazess et al. | 600/449 |
| 6,535,824 B1 * | 3/2003 | Mansky et al. | 506/8 |
| 6,668,230 B2 * | 12/2003 | Mansky et al. | 506/39 |
| 7,660,440 B2 * | 2/2010 | Bourg et al. | 382/110 |
| 8,224,106 B2 * | 7/2012 | Bing et al. | 382/254 |
| 8,225,666 B2 * | 7/2012 | McAleavey | 73/602 |
| 2002/0152813 A1 * | 10/2002 | Dixon et al. | 73/579 |
| 2003/0183011 A1 * | 10/2003 | Hirose | 73/597 |
| 2004/0215075 A1 * | 10/2004 | Zagzebski et al. | 600/442 |
| 2004/0243001 A1 * | 12/2004 | Zagzebski et al. | 600/437 |
| 2006/0173319 A1 | 8/2006 | Sumi | |
| 2006/0184028 A1 * | 8/2006 | Wen | 600/441 |
| 2009/0043545 A1 * | 2/2009 | van Manen et al. | 703/2 |
| 2009/0093721 A1 | 4/2009 | Katsuyama | |
| 2010/0069757 A1 * | 3/2010 | Yoshikawa et al. | 600/454 |
| 2011/0092817 A1 * | 4/2011 | Cloutier et al. | 600/437 |

FOREIGN PATENT DOCUMENTS

| | | |
|---|---|---|
| JP | 2009-101145 | 5/2009 |
| WO | WO 2004/061575 A2 | 7/2004 |

\* cited by examiner (a)

(b)

Fig. 2-2
(a)
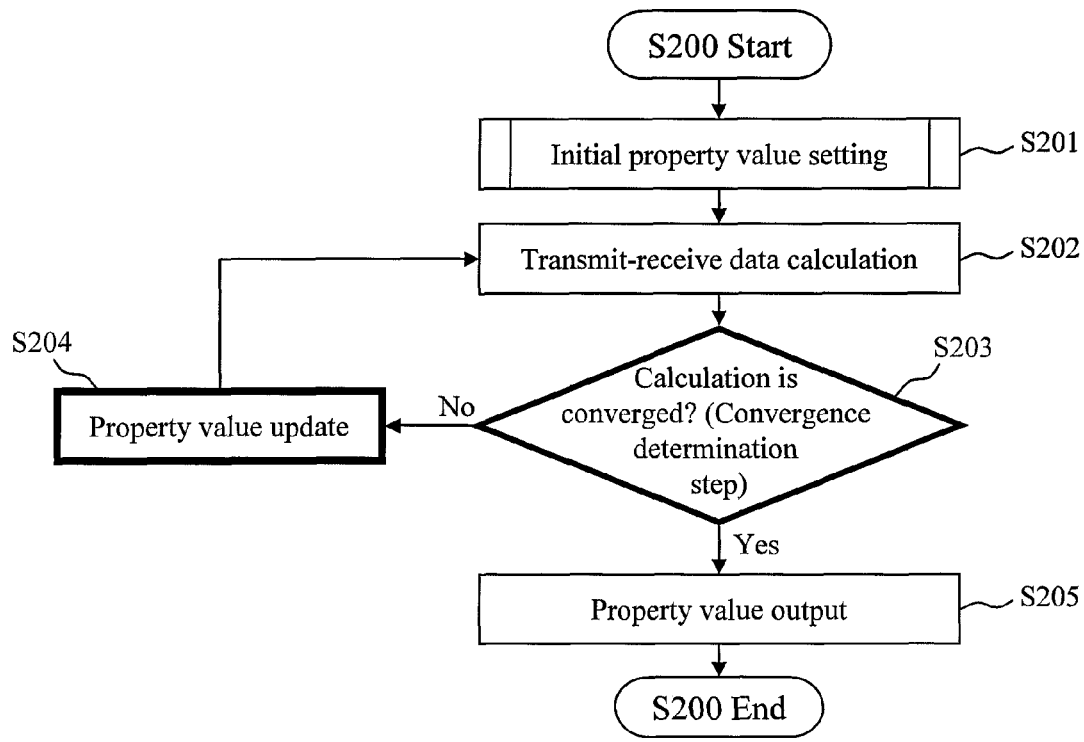
(b)
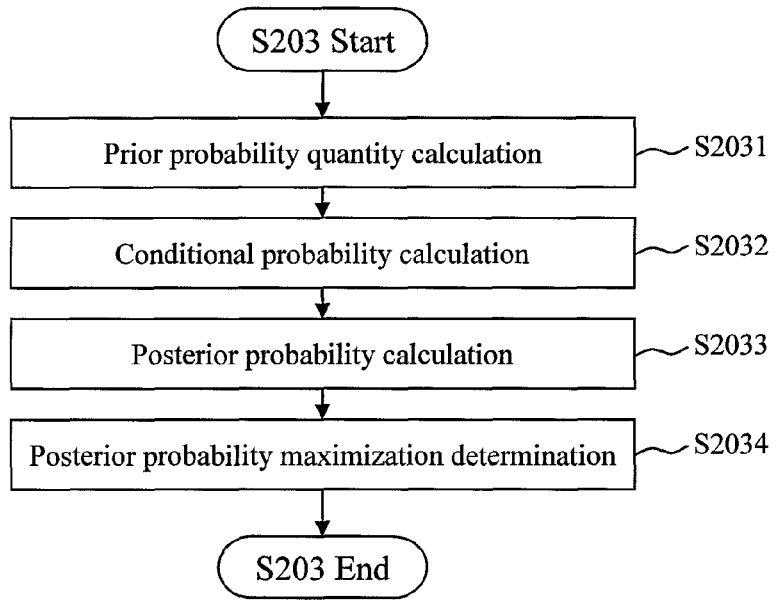

(a)

(b)

Fig. 4-2
(a)
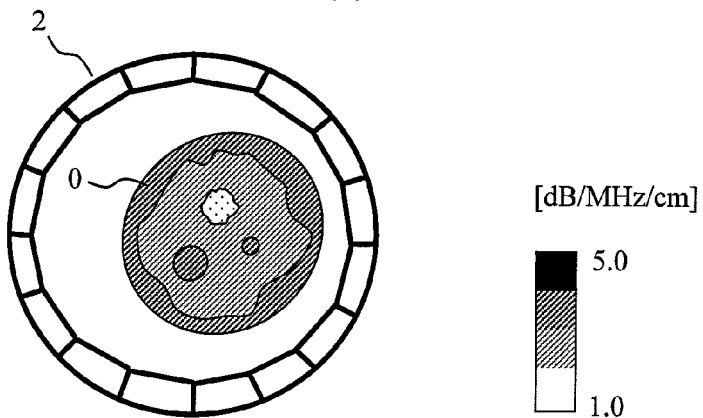
(b)
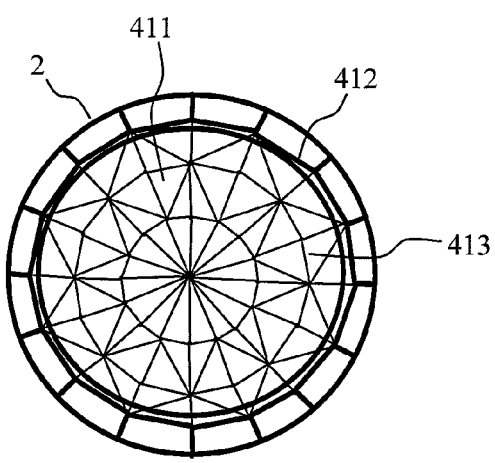
(c)
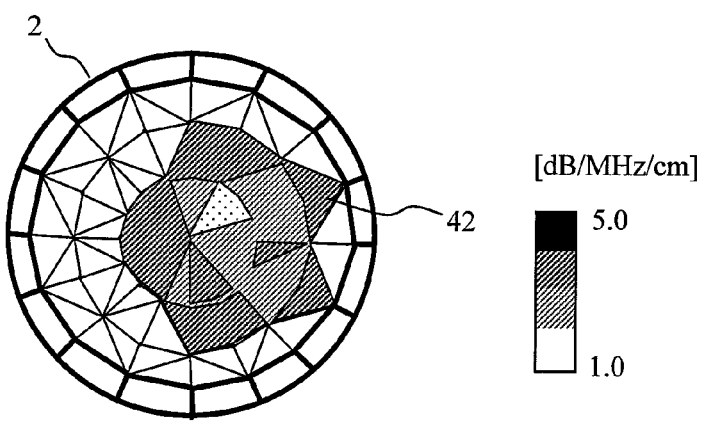

Fig. 5
(a)
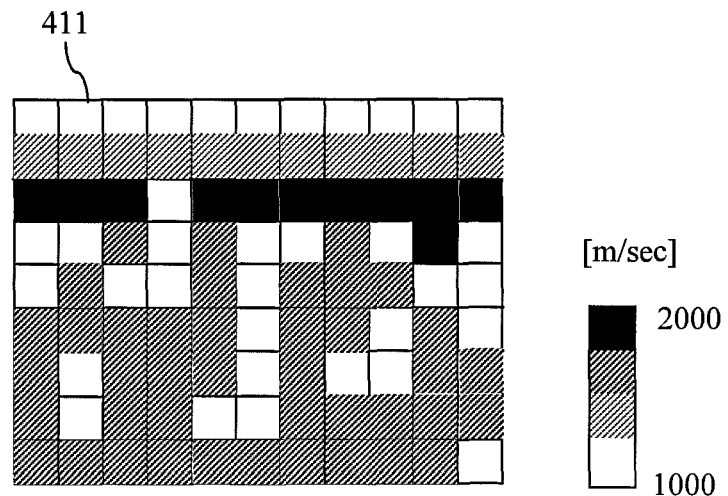
(b)
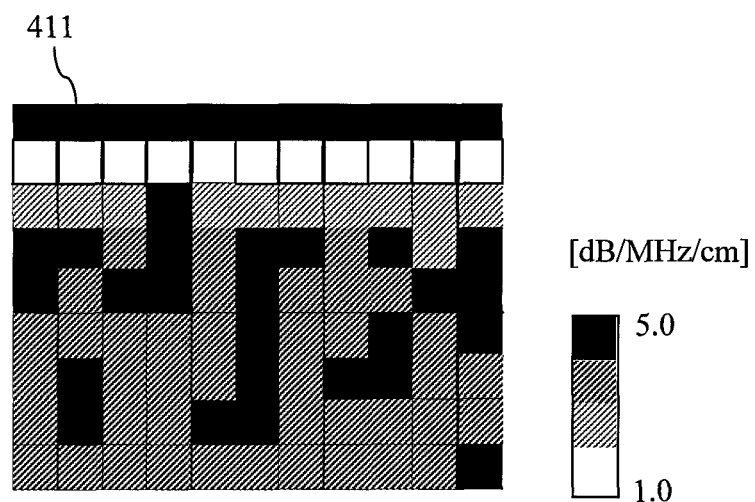

| 3 | 6 | 9 |
|---|---|---|
| 2 | 5 | 8 |
| 1 | 4 | 7 |

(a2)

```
 ┌──8──┬──16──┬──23──┐
 9    10    17     24
 ├──5──┼──14──┼──21──┤
 6     7    15     22
 ├──2──┼──12──┼──19──┤
 3     4    13     20
 └──1──┴──11──┴──18──┘
```

(b1)

| 1 | 2 | 3 | 4 | 5 | 6 | 7 | 8 | 9 |
|---|---|---|---|---|---|---|---|---|
| $\varepsilon_{A1}$ | $\varepsilon_{A2}$ | $\varepsilon_{A3}$ | $\varepsilon_{A4}$ | $\varepsilon_{A5}$ | $\varepsilon_{A6}$ | $\varepsilon_{A7}$ | $\varepsilon_{A8}$ | $\varepsilon_{A9}$ |

(b2)

| 1 | 2 | 3 | 4 | 5 | 6 | 7 | 8 | 9 |
|---|---|---|---|---|---|---|---|---|
| $\varepsilon_{i1}$ | $\varepsilon_{i2}$ | $\varepsilon_{i3}$ | $\varepsilon_{i4}$ | $\varepsilon_{i5}$ | $\varepsilon_{i6}$ | $\varepsilon_{i7}$ | $\varepsilon_{i8}$ | $\varepsilon_{i9}$ |

(b3)

| 1 | 2 | 3 | 4 | 5 | 6 | 7 | 8 | 9 |
|---|---|---|---|---|---|---|---|---|
| $d\varepsilon_{i1}$ | $d\varepsilon_{i2}$ | $d\varepsilon_{i3}$ | $d\varepsilon_{i4}$ | $d\varepsilon_{i5}$ | $d\varepsilon_{i6}$ | $d\varepsilon_{i7}$ | $d\varepsilon_{i8}$ | $d\varepsilon_{i9}$ |

(c1)

| 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
|---|---|---|---|---|---|---|---|---|---|---|---|---|---|---|---|---|---|---|---|---|---|---|---|
| $p_1$ | 0 | $p_3$ | 0 | 0 | $p_6$ | 0 | $p_8$ | $p_9$ | 0 | $p_{11}$ | 0 | 0 | 0 | 0 | $p_{16}$ | 0 | $p_{18}$ | 0 | $p_{20}$ | 0 | $p_{22}$ | $p_{23}$ | $p_{24}$ |

(c2)

| 1 | 2 | 3 | 4 | 5 | 6 | ... | 24 |
|---|---|---|---|---|---|---|---|
| $k(\varepsilon_{A1})\partial_n p_1$ | 0 | $k(\varepsilon_{A1})\partial_n p_3$ | 0 | 0 | $k(\varepsilon_{A2})\partial_n p_6$ | ... | $k(\varepsilon_{A9})\partial_n p_{24}$ |

(d1)

|  | 1 | 2 | 3 | 4 | ... | 24 |  |
|---|---|---|---|---|---|---|---|
| 1 | 1 | 0 | 0 | 0 |  |  | 1 |
| 2 | 0 | $4/6\cdot h^2-4/36\cdot k(\varepsilon_{i1})^2$ | 0 | $-1/6\cdot h^2-2/36\cdot k(\varepsilon)^2$ |  |  | 2 |
| 3 | 0 | 0 | 1 | 0 |  |  | 3 |
| 4 | 0 | $-1/6\cdot h^2-2/36\cdot k(\varepsilon_{i1})^2$ | 0 | $4/6\cdot h^2-4/36\cdot k(\varepsilon)^2$ |  |  | 4 |
|  |  |  |  |  | ... |  | ⋮ |
|  |  |  |  |  |  | ... | 24 |

(d2)

|  | 1 | 2 | 3 | 4 | ... | 24 |  |
|---|---|---|---|---|---|---|---|
|  | $4/6\cdot h^2-4/36\cdot k(\varepsilon_{i1})^2$ | $-1/6\cdot h^2-2/36\cdot k(\varepsilon_{i1})^2$ | $-1/6\cdot h^2-2/36\cdot k(\varepsilon_{i1})^2$ | $-2/6\cdot h^2-1/36\cdot k(\varepsilon_{i1})^2$ |  |  | 1 |
|  | $-1/6\cdot h^2-2/36\cdot k(\varepsilon_{i1})^2$ | $4/6\cdot h^2-4/36\cdot k(\varepsilon_{i1})^2$ | $-2/6\cdot h^2-1/36\cdot k(\varepsilon_{i1})^2$ | $-1/6\cdot h^2-2/36\cdot k(\varepsilon_{i1})^2$ |  |  | 2 |
|  | $-1/6\cdot h^2-2/36\cdot k(\varepsilon_{i1})^2$ | $-2/6\cdot h^2-1/36\cdot k(\varepsilon_{i1})^2$ | $4/6\cdot h^2-4/36\cdot k(\varepsilon_{i1})^2$ | $-1/6\cdot h^2-2/36\cdot k(\varepsilon_{i1})^2$ |  |  | 3 |
|  | $-2/6\cdot h^2-1/36\cdot k(\varepsilon_{i1})^2$ | $-1/6\cdot h^2-2/36\cdot k(\varepsilon_{i1})^2$ | $-1/6\cdot h^2-2/36\cdot k(\varepsilon_{i1})^2$ | $4/6\cdot h^2-4/36\cdot k(\varepsilon_{i1})^2$ |  |  | 4 |
|  |  |  |  |  | ... |  | ⋮ |
|  |  |  |  |  |  | ... | 24 |

Fig. 7
(a1)
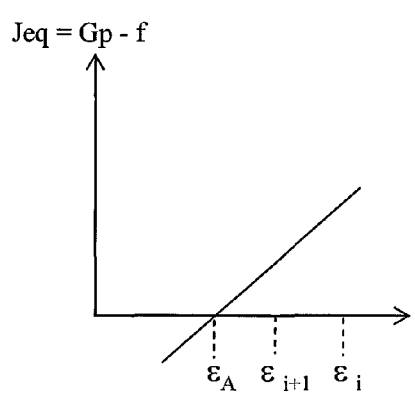
(a2)
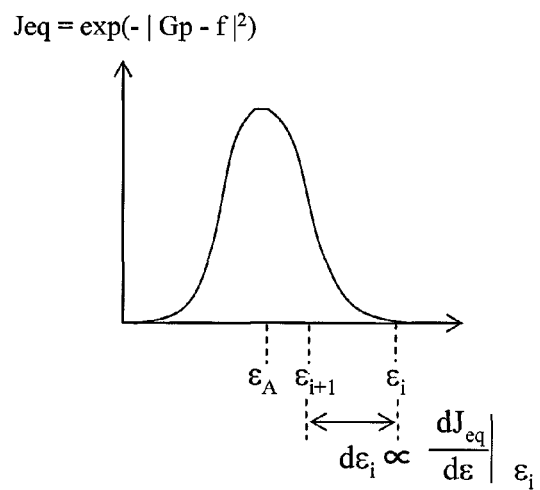
(b)
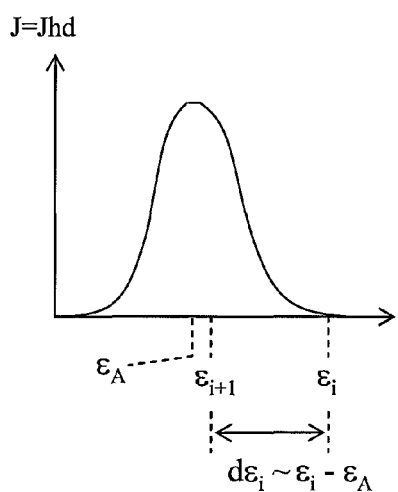
(c)
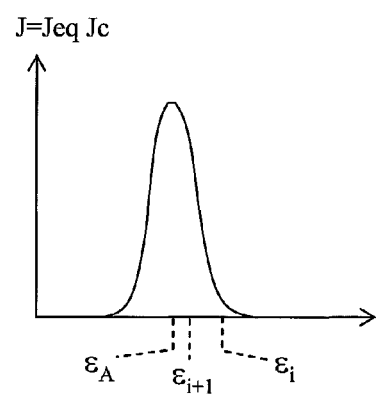

Fig. 8
(a)
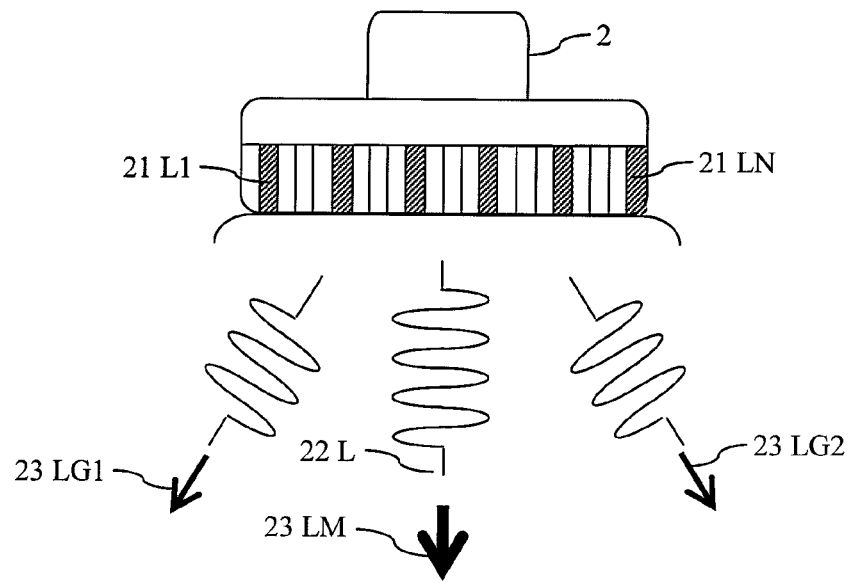
(b)
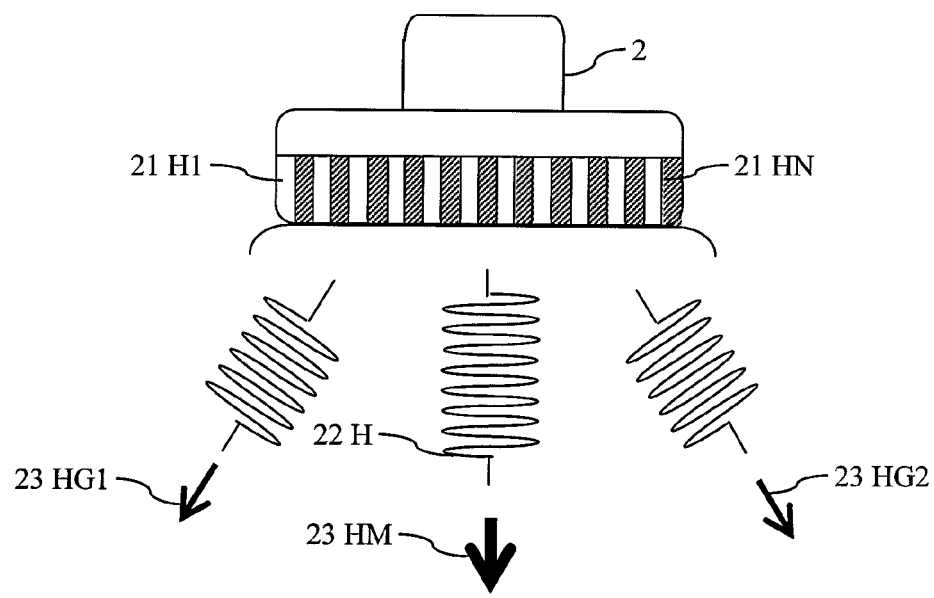

Fig. 9
(a1)
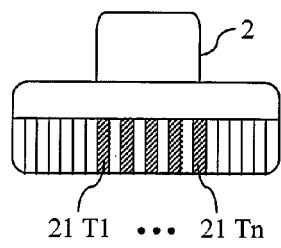
(a2)
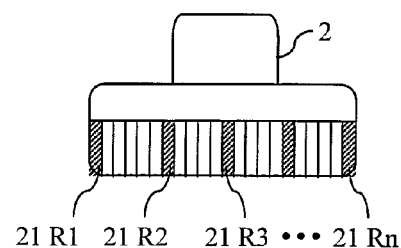
(b1)
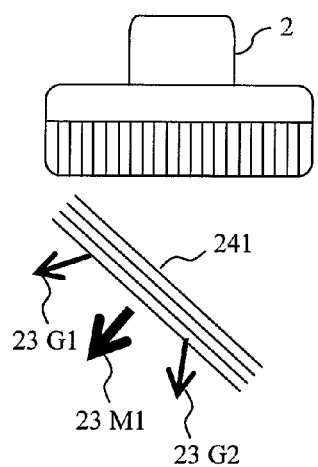
(b2)
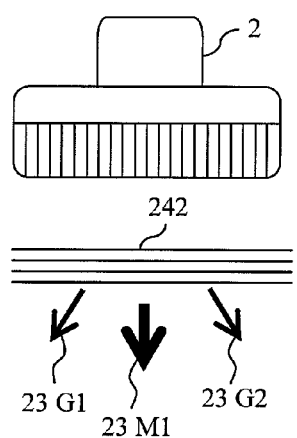
(b3)
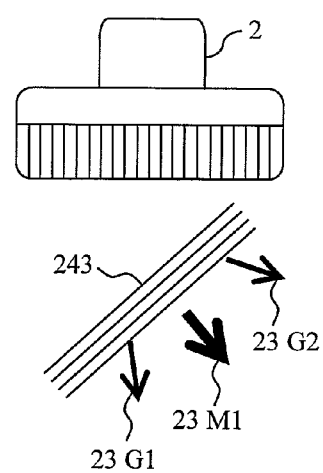

Fig. 13
(a) Method of patent document 1
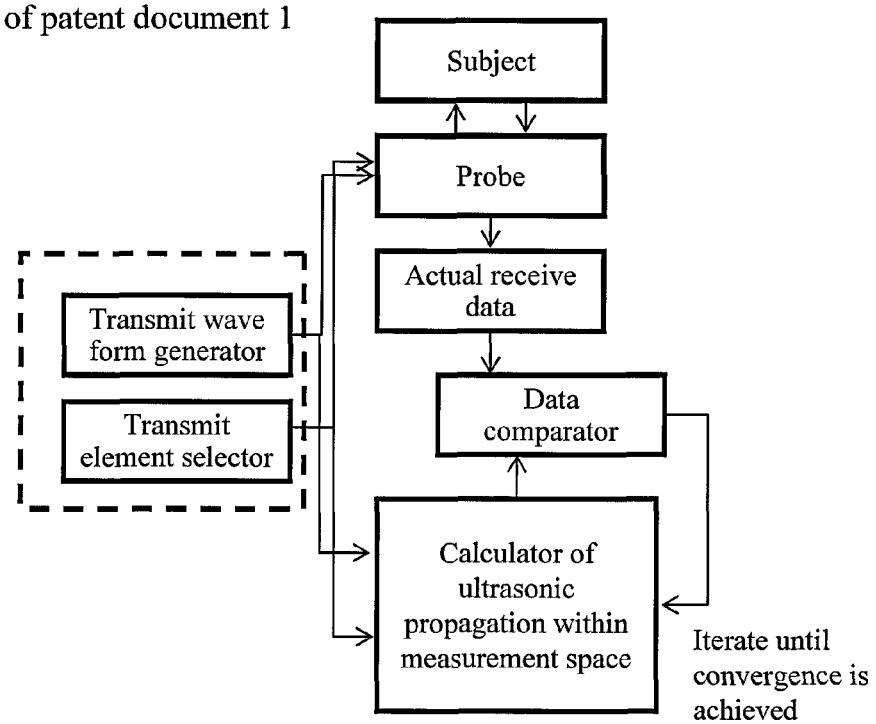
(b) The present invention
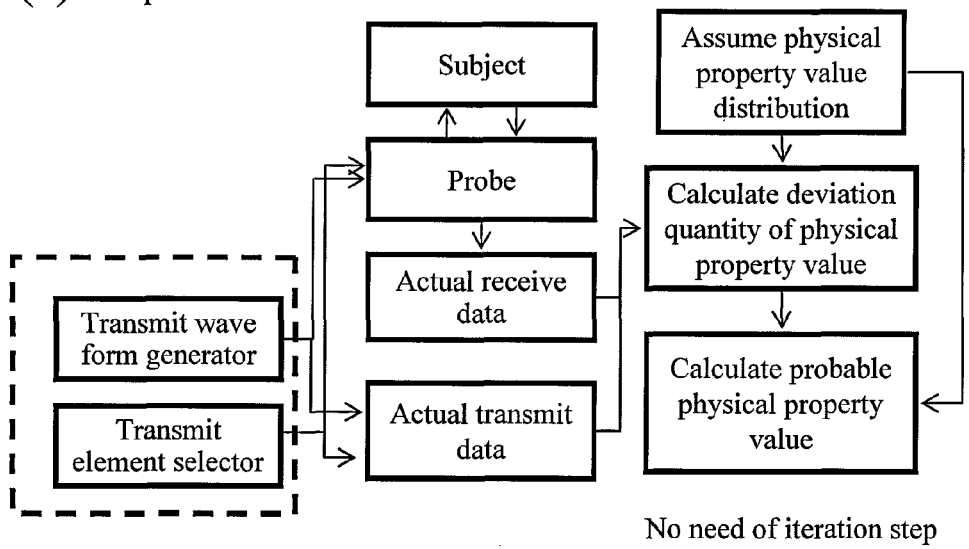

IMAGE RECONSTRUCTION METHOD AND DEVICE

TECHNICAL FIELD

The present invention relates to an image reconstruction method and device of transmitting and receiving signals to and from a measurement region as a measurement object and determining the quantity of a physical property of the measurement region based on the actual receive signal. The present invention relates to a technique with which, even when the distribution of a physical property value such as a density inside the measurement object is non-uniform, the distribution of the physical property value inside the measurement region can be calculated within a feasible period of time without causing image deterioration due to phenomena such as refraction and multiple-reflections caused by the non-uniformity.

BACKGROUND ART

A measuring apparatus is an apparatus to form an image of the interior of a measurement object in non-invasive manner. The measuring apparatus transmits a measurement signal (for example, ultrasonic waves) to the interior of the measurement object from the boundary of the measurement object, and converts a measurement value measured at the boundary into a distribution of physical property value of the interior in accordance with an algorithm based on a physical equation which expresses a propagation phenomenon of the measurement signal. The measurement signal serves as a variable of the physical equation, the physical property values serve as a coefficient and an external force term of the physical equation, and the physical equation is used as an equation expressing a relationship between the measurement signal and the physical property values.

Algorithms for converting a measurement signal into physical property values based on physical equations have been studied as a coefficient identification problem and a boundary value problem in the field of scientific computing. Algorithms actually installed in devices are configured with their conversion accuracy reduced by applying approximation to equations in order to reduce the computation amount to an implementable level. An algorithm in a currently-commercialized product is a method of synthesizing directivities on the basis of an antenna technology, and makes such an approximation that each kind of physical property values of the interior of a measurement object is regarded as uniform. A breast-dedicated system, which is an advanced prototype equipped with a projection mapping algorithm similar to that for CT, also makes such an approximation that the physical property value is regarded as uniform, which means to assume the linearity of a measurement signal.

Moreover, as described in Patent Literature 1, a receive waveform is computed from a transmitted waveform in consideration of the non-uniformity of in-vivo physical property value and in consideration of wave propagation defined by the Helmholtz equation or the like. There is also a method of estimating an in-vivo physical property value by iterating a step of correcting the in-vivo physical property value so that a difference between the measured receive waveform and the calculated receive waveform can be made small.

PRIOR ART DOCUMENTS

Patent Document

PATENT DOCUMENT 1: Domestic Re-publication of PCT International Application No. 2006-511298

Non-Patent Document

NON-PATENT DOCUMENT 1: Breast Imaging using transmission Ultrasound: Reconstructing Tissue Parameters of Sound Speed and Attenuation; Cuiping Li; Duric, N.; Lianjie Huang; BioMedical Engineering and Informatics, 2008. BMEI 2008. International Conference on; Vol. 2 pp. 708-712 (2008)

SUMMARY OF THE INVENTION

Problems to be Solved by the Invention

A Method represented by Non-Patent Literature 1 described above can achieve short processing time because the method is based on approximate equations. In the case where a measurement object has a non-uniform interior structure, however, the method has a problem of being incapable of eliminating, in principle, image deterioration due to phenomena such as refraction and multiple-reflections caused by the non-uniformity.

In addition, the method represented by Patent Literature 1 consumes a time to calculate wave propagation inside a measurement object, and also requires this calculation to be iterated until the difference between the actually-measured receive data and the calculated receive data converges. Hence, the method has a problem of being unpractical when used as a medical apparatus which is required to achieve real-time performance.

The present inventors propose a method and device of transmitting and receiving measurement signals to and from the interior of a measurement object at a boundary of the object, and calculating a physical property value inside the measurement object from the measured value at the boundary, and propose a technique capable of calculating a distribution of physical property value inside the measurement object with an implementable calculation scale, even if the measurement object has a non-uniform internal structure, without having image deterioration due to phenomena such as refraction and multiple-reflections caused by the non-uniformity.

In particular, the present inventors propose a technique of achieving a significant reduction in a calculation scale for estimating a distribution of physical property value from receive data of actual measurement.

Means for Solving the Problem

The present invention obtains a physical property value of a measurement object by using an evaluation quantity derived from physical equations without approximation. The present invention employs a method of estimating a deviation quantity that makes an assumed physical property value closer to a true physical property value, and thereby finding the true physical property value through update of the deviation quantity. Note that it is preferable to use a transmit sequence in which only signals making a large contribution to the image reconstruction are acquired. To be more specific, (a) the present invention proposes an image reconstruction method of transmitting and receiving signals to and from a measurement region as a measurement object and determining a quantity of a physical property of the measurement region through numerical calculation, the method including the following steps:

(1) a transmit-receive data acquisition step (means) of transmitting and receiving signals to and from the measurement region;

(2) a physical property value calculation step (means) of calculating a physical property value from an actual receive signal received from the measurement region; and (3) a physical property value-display value conversion step (means) of converting the physical property value into a display value.

For instance, the physical property value calculation step uses, as an evaluation quantity, a linear sum of: (i) an equation residual quantity that is a residual being a difference between an operator term and an external force term of an equation of motion; (ii) a non-uniformity detection equation residual quantity that is a residual of an equation of detecting non-uniformity of the physical property value by using a matching degree of solutions of the equation of motion under two types of boundary conditions; and (iii) a conditional equation residual quantity that is a residual of a constraint condition, and outputs the physical property value that makes the evaluation quantity be an extremum to the physical property value-display value conversion step (means).

(b) Here, the transmit-receive data acquisition step preferably includes a transmit-receive sequence determination step of determining: (i) the number of times of performing transmissions-and-receptions by transceiver elements, (ii) a spatial layout of the transceiver elements and (iii) transmit-and-receive waveforms, and obtaining results of the transmissions-and-receptions.

In this connection, a receive sequence determination step preferably determines that the number of times of performing transmissions-and-receptions by the transceiver elements is two or more, that the transmit waveform at least includes a plurality of plane burst waves having an equal burst length but having different carrier frequencies within a range of 0.5 MHz to 10 MHz, both inclusive, that the spatial layout of the transmitter elements has spacing inversely proportional to the carrier frequencies, and that a spatial layout of receiver elements is a layout that maximizes an angle of view in the measurement region.

(c) Moreover, the transmit-receive sequence determination step preferably outputs a transmit-receive sequence in which: the number of times of performing transmissions-and-receptions is two or more; and the frequency used in the transmission-and-reception becomes lower as a transmission-and-reception time becomes earlier.

(d) Additionally, the non-uniformity detection equation residual quantity is preferably a residual being a difference between: (i) a differential vector that is a difference between a solution under a Neumann boundary condition and a solution under a Dirichlet boundary condition in a case where a boundary value is actual transmit-receive data, and (ii) a product of a vector expressing the non-uniformity of the physical property value and an operator matrix that is a difference between a Green's function of the equation of motion under a Neumann boundary condition and a Green's function of the equation of motion under a Dirichlet boundary condition in a case where the boundary value is zero.

(e) Further, a conditional equation residual quantity of the evaluation quantity preferably includes at least one of a prior probability quantity that is a prior probability expressing the nature of a distribution of the evaluation quantity of the physical property value, and a low order approximation matching quantity indicating a matching degree with an image reconstructed by a method of synthesizing directivities or projection mapping.

(f) Furthermore, the physical property value calculation step preferably calculates the physical property value that makes the evaluation quantity be an extremum, by using metropolis sampling that is one of stochastic methods.

(g) The evaluation quantity or the equation residual is preferably a residual of any equation among a frequency representation of an elastodynamic equation, a time response representation of the elastodynamic equation and a Helmholtz potential representation value. Moreover, the physical property value is preferably one or more of a Lamé's constant $\lambda$, a Lamé's constant $\mu$, a density of inertia $\rho$, an attenuation coefficient c, ratios therebetween, and a force source f. In addition, the display quantity is preferably any one or more of the $\lambda$, the $\mu$, the $\rho$, the c, and functions thereof including a bulk modulus, a longitudinal wave velocity, a transverse wave velocity, a Poisson's ratio, and a Young's modulus, an impedance, and the force source f.

Effects of the Invention

The present invention uses physical equations without approximation, and thereby enables image reconstruction without having image deterioration due to phenomena such as refraction and multiple-reflections caused by the non-uniformity. Moreover, the processing speed of the image reconstruction is determined depending on a period of time for signal acquisition and a period of time for calculation. In this regard, the period of time for signal acquisition is reduced by use of a transmit sequence in which only signals making large contribution to the image reconstruction are acquired, and the period of time for calculation is reduced by use of the equation of estimating the deviation quantity of the assumed physical property value from the true physical property value. Thus, the present invention achieves a feasible processing period of time of the image reconstruction.

BRIEF DESCRIPTION OF THE DRAWINGS

FIG. 2-1 is a flowchart illustrating a processing flow of an image reconstruction method according to the embodiment.

FIG. 2-2 is a flowchart illustrating the processing flow of the image reconstruction method according to the embodiment.

FIG. 3-1 is a diagram for conceptually explaining a relationship between a measurement object and a probe of the image reconstruction device according to the embodiment.

FIG. 3-2 is a diagram for conceptually explaining a relationship between a measurement object and a probe of the image reconstruction device according to the embodiment.

FIG. 4-1 is a diagram for explaining an outline of processing by a physical property value calculation part of the image reconstruction device according to the embodiment.

FIG. 4-2 is a diagram for explaining an outline of processing by the physical property value calculation part of the image reconstruction device according to the embodiment.

FIG. 5 is a diagram conceptually illustrating a screen presented on a display of the image reconstruction device according to the embodiment.

FIG. 6 is a diagram illustrating one example of data formats of the image reconstruction device according to the embodiment.

FIG. 7 includes diagrams for conceptually explaining a relationship between evaluation quantities and a method of obtaining a physical property in the image reconstruction device according to the embodiment.

FIG. 8 illustrates conceptual diagrams of a basic sequence example of a transmit sequence outputted by a transmit-receive data acquisition part of the image reconstruction device according to the embodiment.

FIG. 9 illustrates conceptual diagrams of one example of a transmit sequence outputted by the transmit-receive data acquisition part of the image reconstruction device according to the embodiment.

FIG. 13 illustrates comparison diagrams of processing blocks between a cited example and the present invention.

MODES FOR CARRYING OUT THE INVENTION

Hereinafter, embodiments of the present invention are described based on the drawings. It should be noted that the details of device configurations and processing operations described below are one example for explaining the present invention. The present invention also includes any combination of the device configurations and processing operations described below, a combination in which an existing technique is added to any of the device configurations and processing operations described below, and a combination in which part of the device configurations and processing operations described below is replaced with an existing technique.

Embodiments

In the first place, an outline of characteristic features of the present invention is described by using FIG. 13. The method described in Patent Literature 1 calculates a receive waveform from a transmitted waveform in consideration of the wave propagation such as the Helmholtz equation and in consideration of the non-uniformity of in-vivo physical property value. This is the method of estimating the in-vivo physical property value by iterating a step of correcting the in-vivo physical property value so that the difference between the actually-measured receive waveform and the calculated receive waveform can be made small. The device configuration and the processing flow thereof are illustrated in part (a) of FIG. 13.

On the other hand, the present invention employs a configuration in part (b) of FIG. 13, and calculates, in only one calculation step, a deviation quantity between a probable physical property value and an assumed physical property value from actual transmit-receive data and a distribution of the assumed physical property value. Then, a sum of the deviation quantity and the assumed physical property value is outputted as the probable physical property. This calculation achieves large improvement of the calculation scale, which is large scale in Patent Literature 1. If the only one calculation step arouses concern about the reliability due to influence of noise and the like, a method of iterating the calculation within a number of times not impairing the real-time performance is also effective to improve the reliability, as a matter of course.

(Configuration of Image Reconstruction Apparatus)

Figure 1:
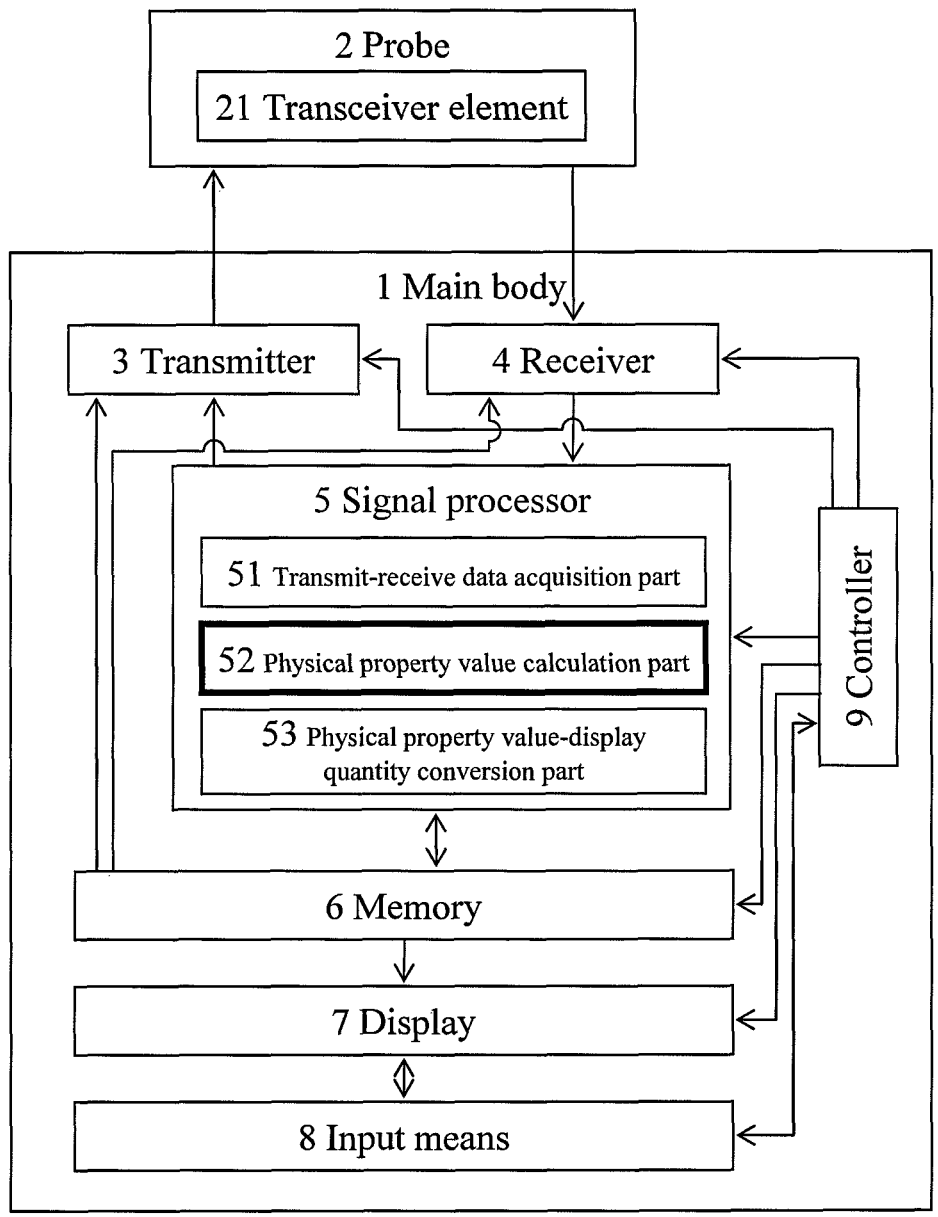
FIG. 1 is a diagram illustrating a block configuration of an image reconstruction device according to an embodiment.

Hereinafter, an embodiment is explained with reference to FIG. 1 to FIG. 11. FIG. 1 is a block diagram illustrating a configuration of an image reconstruction device of the present invention. The image reconstruction device according to the embodiment includes a main body 1 and a probe 2. The main body 1 according to the embodiment has a computer configuration and implements numerical calculations and other signal processing through a computer program.

The probe 2 includes multiple transceiver elements 21. The main body 1 includes a transmitter 3, a receiver 4, a signal processor 5, a memory 6, a display 7, an input means 8, and a controller 9. The signal processor 5 further includes: a transmit-receive data acquisition part 51 transmitting and receiving measurement signals to and from a measurement region, and outputting an actual receive signal that is the signal thus received; a physical property value calculation part 52 receiving the actual receive signal from the transmit-receive data acquisition part, converting the actual receive signal into a physical property value of the measurement region, and outputting the physical property value; and a physical property value-display quantity conversion part 53 receiving the physical cal property value from the physical property value calculation part and converting the physical property value into a display quantity. The physical property value calculation part 52 indicated by a thick frame in FIG. 1 provides a particularly important processing function among processing functions proposed in this application.

(Measurement Operations of Image Reconstruction Apparatus)

The image reconstruction device according to the embodiment performs signal processing in the following procedure.

Firstly, the transmit-receive data acquisition part 51 of the signal processor 5 determines a transmit sequence that is composed of transmission waveforms for the respective transceiver elements 21. The determined transmit sequence is outputted directly to the transmitter 3 from or is written to the memory 6 by the transmit-receive data acquisition part 51. The transmit sequence written in the memory 6 is read from the memory 6 and outputted to the transmitter 3 at predetermined timing.

Next, an operator performing the measurement operation while viewing a display screen of the display 7 performs manual input for start of imaging of a measurement region by using the input means 8 such as a mouse, a keyboard, an operation bottom or another means. Upon detection of the manual input, the input means 8 outputs an imaging start signal to the controller 9. Upon receipt of the imaging start signal, the controller 9 notifies the signal processor 5 of the start of imaging processing.

Upon receipt of the transmit sequence from the signal processor 5 or the memory 6, the transmitter 3 sends the signals to the measurement object from the transceiver elements 21 corresponding to the transmit sequence. For instance, ultrasonic signals are transmitted to an imaging subject such as a living body.

At the same time as the transmission start of the transmit sequence, the receiver 4 receives, via the transceiver elements 21, receive signals corresponding to signals reflected from the imaging subject or transmitted through the imaging subject. The receiver 4 outputs the receive signals from the respective transceiver elements 21 to the signal processor 5.

The signal processor 5 firstly receives, at the transmit-receive data acquisition part 51, the transmit-receive data from the respective transceiver elements 21. Then, the signal processor 5 calculates, at the physical property value calculation part 52, physical property values such as Lamé's constants $\lambda$, $\mu$, and a density of inertia $\rho$ on the basis of the transmit-receive data from the respective transceiver elements 21. Subsequently, the signal processor 5 converts the physical property values such as the Lamé's constants and the density of inertia $\rho$ into display quantities of the physical property values to themselves, or other values such as a longitudinal wave velocity $(\lambda+2\mu)/\rho$, a transverse wave velocity $\mu/\rho$, and a bulk modulus $(\lambda+2\mu)/\rho$ and outputs the display quantities to the memory 6.

The memory 6 outputs the written display quantities to a monitor or the like of the display 7. The display 7 shows the display quantities corresponding to the physical property values on the screen.

(Outline of Processing Operation)

Figure 2:
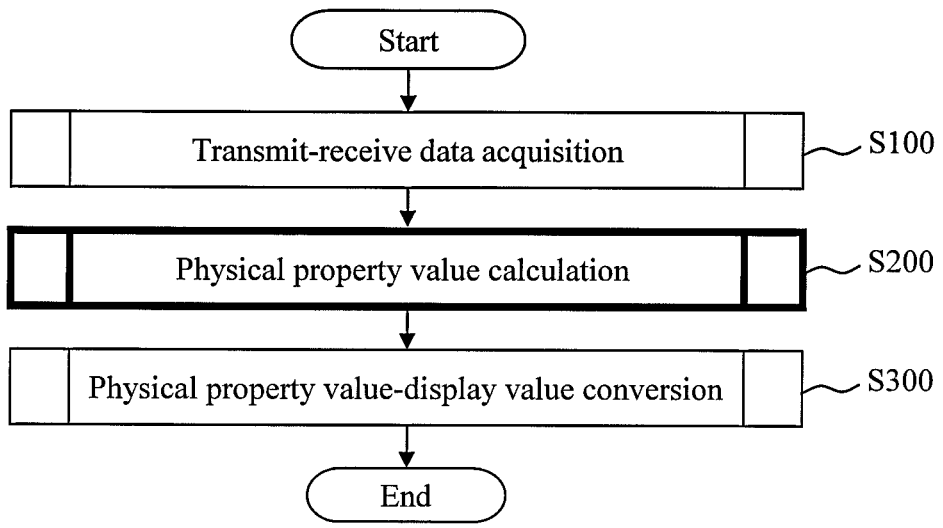
Figure 1:
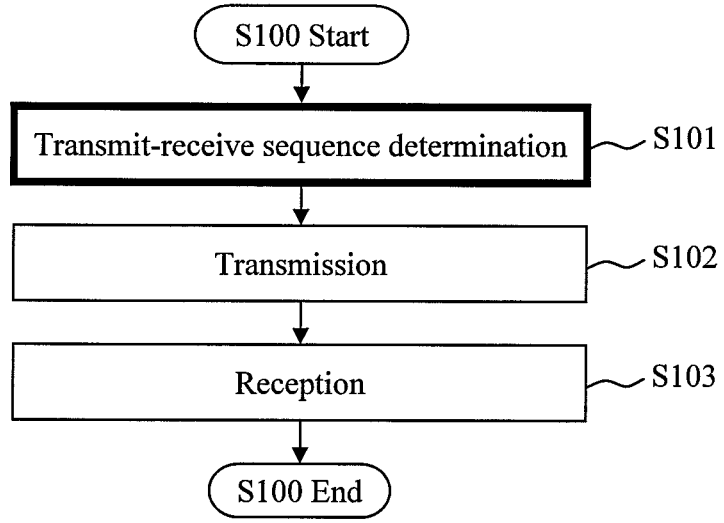

FIG. 2-1 illustrates a flowchart for explaining a processing flow of an image reconstruction method according to the present embodiment. Steps forming the image reconstruction method are executed through numerical calculations at a numeric calculation unit of a measurement device (for example, a computer). The numerical values and calculation results used in these steps are stored in a storage area (memory). These numerical values are exchanged between the numeric calculation unit and the storage area (memory) according to instructions from the program along with the progress of the numeric calculations.

Part (a) of FIG. 2-1 illustrates an outline of the processing of the image reconstruction method, and part (b) of FIG. 2-1 illustrates specific processing details in step S100.

As illustrated in part (a) of FIG. 2-1, the image reconstruction method according to the present embodiment includes a transmit-receive data acquisition step (S100), a physical property value calculation step (S200), and a physical property value-display quantity conversion step (S300). The transmit-receive data acquisition step (S100) includes transmitting and receiving measurement signals to and from the measurement region, and outputting the actual receive signals, which are received signals, to the physical property value calculation step. The physical property value calculation step (S200) includes calculating physical property values of the measurement region from the above actual receive signals, and outputting the calculated values to the physical property value-display quantity conversion step. The physical property value-display quantity conversion step (S300) includes executing processing of converting the above physical property values into the display quantities. The physical property value calculation step (S200), indicated by a thick frame in the drawing, provides a particularly important processing function among the processing functions proposed in this application.

(Details of Transmit-Receive Data Acquisition Step)

Part (b) in FIG. 2-1 illustrates processing details of the transmit-receive data acquisition step (S100). The transmit-receive data acquisition step (S100) includes a transmit-receive sequence determination step (S101), a transmission step (S102), and a reception step (S103). The transmit-receive sequence determination step (S101) includes executing processing of determining conditions of a transmit-receive sequence. The transmission step (S102) includes executing processing of transmitting measurement signals (for example, ultrasound waves) to a measurement region. The reception step (S103) includes receiving the receive signals from the measurement region. The transmit-receive sequence determination step (S101), indicated by a thick frame in the drawing, determines numerical conditions for improving the efficiency of the numerical calculation in the physical property value calculation step (S200).

(Details of Physical Property Value Calculation Step)

Part (a) of FIG. 2-2 illustrates processing details of the physical property value calculation step (S200). The physical property value calculation step (S200) uses an evaluation quantity J, which is to be described later, for the numerical calculation of the physical property values. In the case of the present embodiment, a physical property value of the interior of the measurement object is obtained as an extremum of an evaluation quantity J.

Upon start of the physical property value calculation step (S200), an initial value of a physical property value is set in an initial physical property value setting step (S201). Then, a transmit-receive data calculation step (S202) calculates an actual receive signal that is a receive signal corresponding to the initial value of the physical property value. The subsequent convergence determination step (S203) determines whether or not the calculation result is converged depending on whether or not the evaluation quantity J is an extremum. When the determination result in the step (S203) is negative (No), the physical property value update step (S204) updates the physical property value, and returns to the calculate-and-receive data calculation step (S202) for the updated physical property value. This loop processing is iterated until the determination result in the step (S203) becomes affirmative (Yes). The physical property value in the case where the determination result in the step (S203) is affirmative (Yes) is outputted to the physical property value-display quantity conversion step (S300). The convergence determination step (S203) and the physical property value update step (S204), indicated by thick frames among the processing steps illustrated part (a) of FIG. 2-2 are a step including new processing. This step includes processing for obtaining an evaluation quantity J and its extremum.

In the case of the present embodiment, the "evaluation quantity" is given as a linear sum of (1) an equation residual quantity that is a residual being a difference between an operator term and an external force term of an equation of motion, (2) a non-uniformity detection equation residual quantity that is a residual of an equation of detecting the non-uniformity of physical property value depending on the matching degree between solutions of the equation of motion under two types of boundary conditions, and (3) a conditional equation residual quantity that is a residual of a constraint condition. It should be noted that the evaluation quantity may be given as any one of these residual quantities, a linear sum or a product of plural ones of them, or an exponential function including them as exponents.

(Details of Evaluation Quantity)

The following provides explanation of details of the evaluation quantity. First of all, the explanation is provided for a case where whether or not the evaluation quantity J is converged is determined depending on whether the evaluation quantity J takes an extremum (zero in this embodiment). This determination, however, is equivalent to maximizing $P=\exp(-J^2)$ that is an exponential function of the "non-uniformity detection equation residual quantity" J. In other words, the calculus of variations using the evaluation quantity J can be also expressed as processing of maximizing an exponential function P representing a probability density.

In the case where the measurement signals are ultrasonic waves, an equation of motion is given using a frequency representation of an elastodynamic equation, a time response representation of the elastodynamic equation or a Helmholtz potential representation of the elastodynamic equation. In this case, the physical property values are a Lamé's constant $\lambda$, a Lamé's constant $\mu$, and a density of inertia $\rho$. In the case where a measurement region is a human body, the initial physical property values λ and ρ are given as 2e9 [kg/m/sec^2] and 1e3 [kg/m^3], respectively, which are set to be uniform within the entire measurement region.

Firstly, a basic evaluation quantity is explained. The basic evaluation quantity is a residual being a difference between an operator term and an external force term of an equation of motion and is called as an equation residual quantity $J_{eq}$. Here, in the equation of motion, the operator is expressed by a matrix G(ϵ)[i][j], a displacement is expressed by a vector p, and the external force is expressed by a vector f, where G is a function of a physical property value ϵ to be obtained. In this case, a relationship G*p=f holds among these quantities. Hence, if the equation residual quantity $J_{eq}$ is defined as $J_{eq}$=G*p−f, $J_{eq}$ is a function of the physical property value ϵ, and the equation residual quantity $J_{eq}$ is 0 when $ϵ_A$ is a true value. A generally-known method may be used as a method of obtaining the physical property value $ϵ_A$ that makes the equation residual quantity be 0. For instance, use of the method of steepest descent with $J_{eq}$=−(G*p−f)$^2$ or the like can be cited as one example.

By use of this evaluation quantity $J_{eq}$, a solution satisfying an ideal (not-approximated) physical equation can be obtained as a physical property value that gives the extremum (zero in this embodiment) of the evaluation quantity J. In addition, influences of refraction and scattering can be eliminated from the physical property value thus obtained.

Next, an evaluation quantity for obtaining a physical property value at high speed is explained.

The boundary conditions of the equation of motion are two types, that is, the Neumann condition and the Dirichlet condition. Here, for the equation of motion having a set physical property value as a coefficient, a solution under the Neumann condition (the boundary value=the actual transmit-receive data) is denoted by h1, and a solution under the Dirichlet condition (the boundary value=the actual transmit-receive data) is denoted by d1. In addition, for the equation of motion having the set physical property value as the coefficient, a solution under the Neumann condition (the boundary value=0; the non-uniformity is taken into account) is denoted by h2, and a solution under the Dirichlet condition (the boundary value=0; the non-uniformity is taken into account) is denoted by d2. In this case, the solution obtained in consideration of the non-uniformity with the actual transmit-receive data used as the boundary value is given as h1+d1 under the Neumann condition or as h2+d2 under the Dirichlet condition. If the non-uniformity is estimated precisely, the two conditions match with each other. That is to way, h1+d1=h2+d2 holds.

For this reason, in this description, the evaluation quantity J defined as the following equation the solution of which is 0 if the non-uniformity is estimated precisely is used as an equation of detecting the non-uniformity of the physical property value depending on the matching degree between the solutions of the equation of motion.

$$J_{dh}=(-h1+h2)-(d1-d2) \quad (1)\ \text{Equation}$$

This evaluation quantity J ($J_{dh}$) serves as a "non-uniformity detection equation residual quantity" in Claims.

Here, σ denotes a quantity indicating a difference between a set value and a true value of the Lamé's constant λ, and μ denotes a quantity indicating a difference between a set value and a true value of the density of inertia ρ. By using a matrix representation GN[i][j] of a Green's function of the equation of motion under the Neumann condition (this is configured in the same manner with a method such as the finite element method), and the matrix representation GD[i][j] of the Green's function of the equation of motion under the Dirichlet condition, the second quantity on the right side of (1) Equation (i.e., d1−d2) can be expressed as a product of a matrix (GD$^{-1}$·GN$^{-1}$) and a vector (σ, μ).

In the present embodiment, a deviation quantity $dϵ_i$ of the physical property value is calculated (deviation quantity estimation step) by using the following relation derived for σ based on the foregoing relation:

$$GN(dϵ_i)*(h1+d1)=σ \quad (2)\ \text{Equation,}$$

and the set value $ϵ_i$ of the physical property value is sequentially updated to $ϵ_{i+1}=ϵ_i+dϵ_i$ (physical property value update step). The deviation quantity $dϵ_i$ herein is a value relative to the initial value $ϵ_{i0}$ of the physical property value. The derivation of the (2) Equation is described in details later.

The setting and update of the physical property value (S204) are iterated until the fulfillment of a condition (S203), for a set minute quantity e, in which the evaluation quantity $J_{dh}(ϵ_i)$ having as a variable the physical property value $ϵ_i$ updated by an i-th update can be regarded as 0 (i.e., $|J_{dh}(ϵ_i)|<e$), or in which the exponential function $\exp(-|J_{dh}(ϵ_i)|^2)$ of the evaluation quantity can be regarded as maximum (i.e., $|\exp(-|J_{dh}(ϵ_{i+1})|^2)-\exp(-|J_{dh}(ϵ_i)|^2)|<e$). Then, the set value of the physical property value taken when the condition (convergence condition) is fulfilled is used as an estimated value for output of the physical property value calculation step (S205). Note that, the evaluation quantity J is calculated from the transmit-receive data (S202).

By use of this evaluation quantity J, the solution satisfying the ideal (not-approximated) physical equation can be obtained as the physical property value that gives the extremum (zero in this embodiment) of the evaluation quantity J. In addition, the influences of refraction and scattering can be eliminated from the physical property value thus obtained. Moreover, the physical property value can be obtained within a short calculation period of time.

Next, description is provided for a case where the convergence determination step (S203) is executed as processing of maximizing the exponential function P. When a constraint condition includes a prior probability, the convergence determination step (S203) can be expressed as in part (b) of FIG. 2-2. This determination processing includes a prior probability calculation step (S2031), a conditional probability calculation step (S2032), a posterior probability calculation step (S2033), and a posterior probability maximization determination (S234).

Here, "c" denotes a physical property value within a measurement region, and "lc" denotes a linear process that takes a value "1" at a discontinuous portion and takes a value "0" at a continuous portion. In this case, a prior probability quantity Jc expressing an assumption that the physical property value distribution is composed of a domain in which constant values continue and its boundary in space can be expressed as, the following equation:

$$Jc=(\nabla c)^2(1-lc)+lc \quad (3)\ \text{Equation.}$$

This prior probability quantity Jc serves as the "conditional equation residual quantity" Jc in Claims. The prior probability quantity Jc can be also expressed as an exponential function Pc=exp(−Jc^2) as in the case with the "non-uniformity detection equation residual quantity" J. When the physical property value is calculated with the prior probability quantity introduced as described above, an information quantity necessary for the calculation of the physical property value can be complemented. Hence, even if there is a shortage of measurement points, the physical property value in the measurement region can be calculated. Note that the evaluation quantity in the case where the evaluation quantity J is complemented by the prior probability quantity Jc is given as $J^2+Jc^2$ or $P*Pc(=\exp(-(J^2+Jc^2))$.

Here, the evaluation quantity J is given as a primary expression of receive data, and the exponent $(-J^2)$ of the exponential function P is given as a secondary expression of the receive data. A calculation of an inverse matrix generally requires a long period of time. When each function is a primary or secondary expression, however, the Sherman-Morrison formula, the Woodbury formula or any other perturbation expansion formula for a matrix can be applied to a small change in the matrix (GN-GD) associated with a small change in the physical property value in step S204, and accordingly the calculation amount required to update the calculation result of the evaluation quantity J can be reduced. Specifically, a significant reduction in the time for the calculation of the inverse matrix leads to a reduction in the time for the whole calculation of the evaluation quantity J.

The foregoing description is provided for the case where the quantity (conditional equation residual quantity) in which the conditional expression assisting the calculation of the physical property value is reflected is expressed by using the prior probability quantity Jc. Instead, it is also possible to define a low order approximation matching quantity using an image calculated by a conventional image reconstruction method as a complement, and to define the aforementioned "conditional equation residual quantity" Jc as a sum of the prior probability quantity and the low order approximation matching quantity.

More specifically, the prior probability calculation step S2031 may include (1) the prior probability quantity calculation step, and (2) a low order approximation matching quantity calculation step. Here, the low order approximation matching quantity calculation step may include (1) an image formation step of forming an image of a physical property value distribution c' by the directivity synthesizing method, projection mapping or any other conventional method; and (2) a low order approximation matching quantity calculation step of calculating a low order approximation matching quantity that is a secondary expression $(c-c')^2$ of a difference $(=c-c')$ between the physical property value distribution c assumed in the physical property value update step S204 and a physical property value distribution c' (image) obtained by the conventional method. Then, the "conditional equation residual quantity" Jc may be calculated as a sum of the prior probability quantity and the low order approximation matching quantity:

$$Jc=(\nabla c)^2(1-lc)+lc+(c-c')^2 \quad (4) \text{ Equation.}$$

The foregoing description is provided for the method of obtaining the physical property value that minimizes the linear sum of secondary expressions of $J^2+Jc^2$ specified by the "non-uniformity inspection equation residual quantity" J and the "conditional equation residual quantity" Jc or that maximizes the exponential function $P*Pc=\exp(-(J^2+Jc^2))$ specified by these two residual quantities. Instead, the evaluation quantity may include an equation residual quantity Je that is given as a secondary expression of a difference between the right side and the left side of an equation of motion. In this case, the physical property value may be obtained which minimizes a linear sum of secondary expressions of $J^2+Jc^2+Je^2$, or maximizes the exponential function $P*Pc*Pe=\exp(-(J^2+Jc^2+Je^2))$.

In the present invention, if the conditional equation residual quantity of the evaluation quantity includes at least one of: the prior probability quantity that is a prior probability indicating the nature of a physical property value distribution; and the low order approximation matching quantity that indicates the matching degree with an image reconstructed by a method of modeling receive signals by use of the directivity synthesizing method or projection mapping, the introduction of the prior probability can complement the information quantity. Thus, even if there is a shortage of measurement points, the physical property value in the measurement region can be calculated.

Moreover, the aforementioned matrix (GN-GD) is not a full rank matrix. For this reason, $(\sigma^*, \mu^*)$ that is a solution to the matrix (GN-GD)×vector$(\sigma, \mu)=0$ is a variable quantity. Hence, one possible example of the above physical property value update step (S204) is to update the physical property value by sampling this variable quantity.

When an update value candidate $(\sigma', \mu')$ of the physical property value is stochastically sampled, the current physical property value $(\sigma, \mu)$ can be updated to an updated value according to the following equation:

$$P(\sigma,\mu \to \sigma',\mu')=\min(1, P(\sigma,\mu)/P(\sigma',\mu')) \quad (5) \text{ Equation.}$$

Here, $P(\sigma, \mu)$ is $\exp(-J\sigma, \mu^2-J)$, and $P(\sigma', \mu')$ is $\exp(-J\sigma', \mu'^2-J)$. This update rule is called as the metropolis sampling method. The execution of the above processing makes the calculation scale small.

Example 1

Placement Example of Probe and Display Example of Measurement Result

Figures 1, 3:
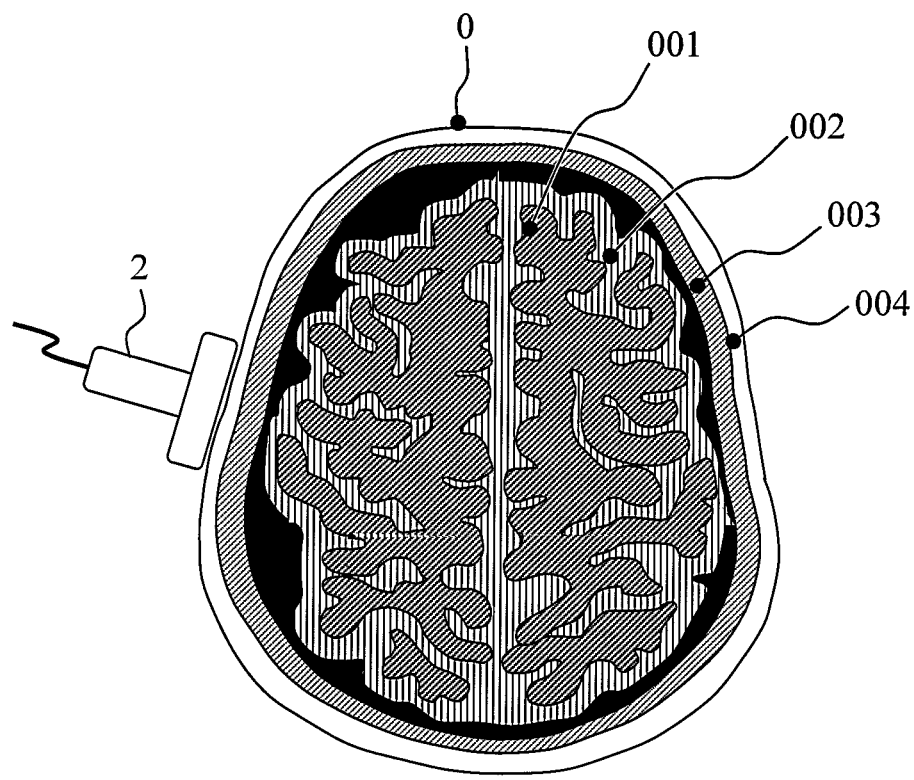
Figure 3:
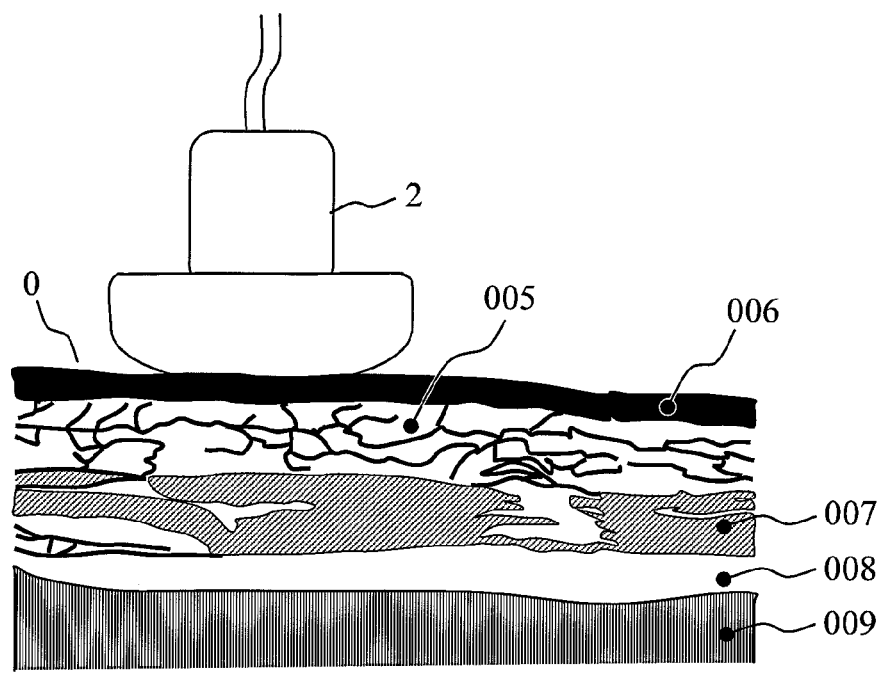
Figure 2:
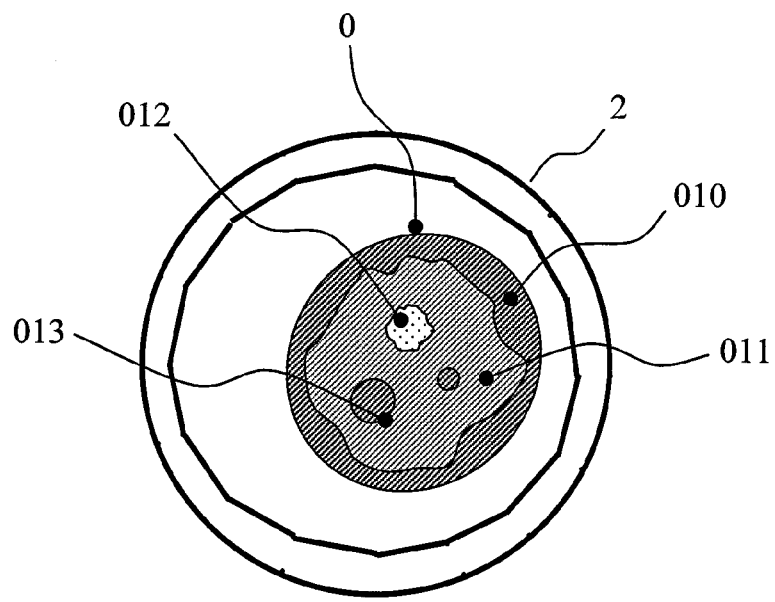

Hereinafter, description is provided for a case where the foregoing image reconstruction device is used to measure the interior of a human body. FIG. 3-1 and FIG. 3-2 are diagrams each for explaining conceptually a mode of measuring a measurement object by using the probe 2. FIG. 3-1 illustrates a case where the measurement region is the brain of a human, part (a) of FIG. 3-2 illustrates a case where the measurement region is the abdominal region of a human, and part (b) of FIG. 3-2 illustrates a case where the measurement region is a breast of a human.

In these drawings, "001" to "013" are internal structures that cause the non-uniformity. Incidentally, "001" is a cerebral gray matter, "002" is a cerebral white matter, "003" is the skull, "004" is an epithelium, "005" is a fat, "006" is an epithelium, "007" is a muscle, "008" is a body cavity, "009" is an organ, "010" is an epithelium, "011" is a fat, "012" is a fibroma, and "013" is a cancerous tissue. The placement position of the probe 2 on a space may be a part of the boundary of the measurement region as illustrated in FIG. 3-1 and part (a) of FIG. 3-2, or may be the entire boundary of the measurement region as illustrated in part (b) of FIG. 3-2. Here, the reference numeral "0" in the drawings indicates a measurement object.

Figures 1, 4:
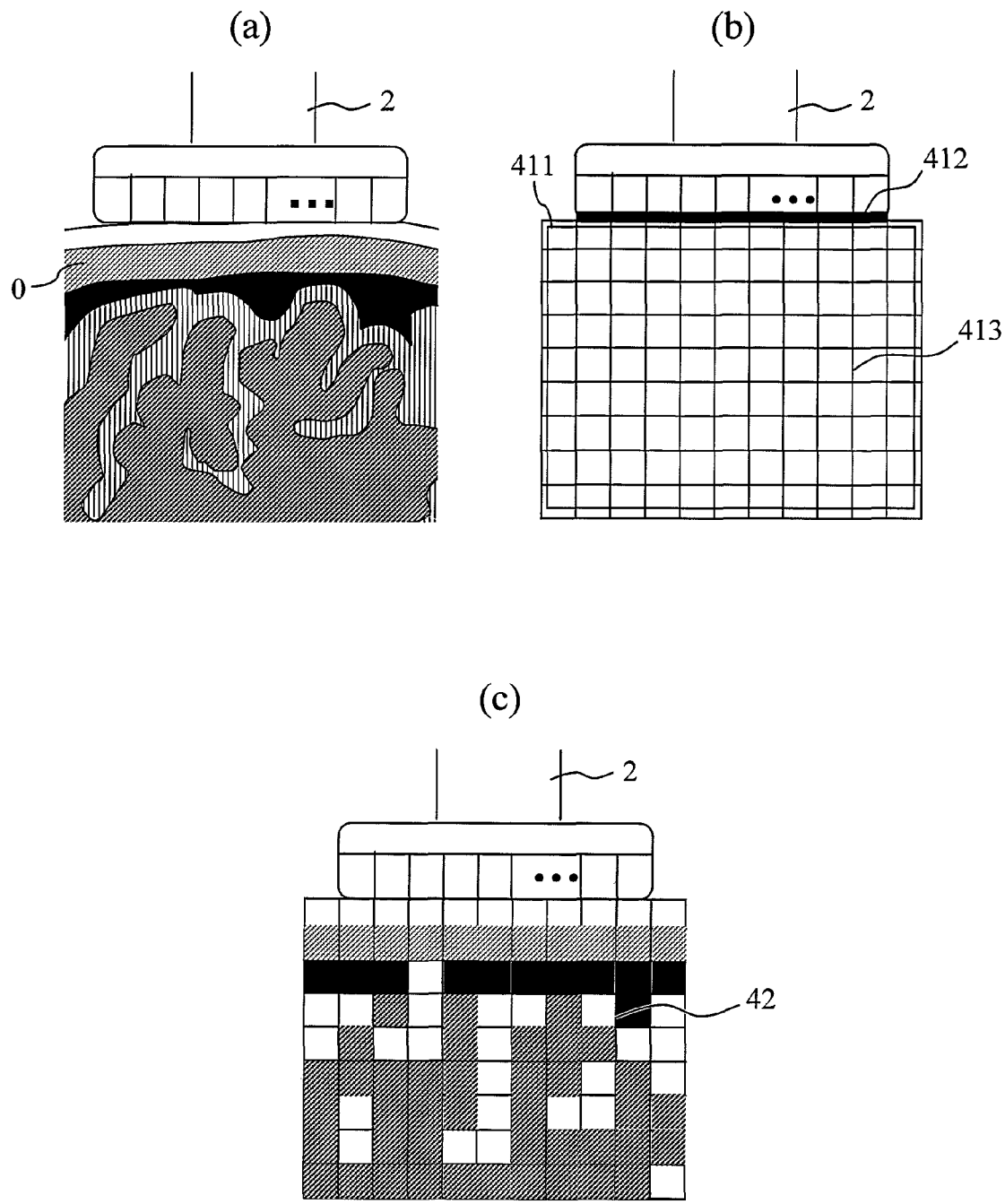

FIG. 4-1 illustrates diagrams for explaining the outline of processing by the physical property value calculation part 52. Part (a) of FIG. 4-1 illustrates a state where the probe 2 is in contact with part of the boundary of a measurement object 0. The evaluation quantity to be used to evaluate the internal structure of the measurement object 0 is calculated by using the equation of motion. Based on the assumption that a space of the measurement object is divided into small cells in the same manner as the finite element method and the boundary element method, the equation of motion is formed by defining a variable of the equation for a nodal point of each cell, and by defining a coefficient of the equation for each cell.

The physical property value calculation part 52 sets a measurement region 411 for numerical calculation within a space in the measurement object as illustrated in part (b) of FIG.

4-1. In the drawing, the measurement region 411 is given as a region having a rectangular cross section in a certain size relative to a transmit-receive surface of the probe 2. Next, the physical property value calculation part 52 sets a boundary 412 where actual receive data can be obtained within the measurement region 411. In part (b) of FIG. 4-1, the boundary 412 is set at a layout range of the transceiver elements 21 in the probe 2. Moreover, the physical property value calculation part 52 virtually divides the inside of the measurement region 411 into small cells 413. In the drawing, the length of a horizontal side of each cell 413 is set equal to the length of the transceiver element 21. Additionally, in the drawing, the length of a side of the cell 413 in a depth direction is set equal to the length of the horizontal side. The length of each side can be determined according to measurement ability. Part (c) of FIG. 4-1 is a diagram in which a variation in the physical property value 42 that makes the evaluation quantity of each cell 413 be an extremum is expressed by a density difference among the cells.

Parts (a) to (c) of FIG. 4-2 correspond to parts (a) to (c) of FIG. 4-1. However, FIG. 4-2 depicts an example in which the transceiver elements 21 are placed in such an annular form as to surround the entire boundary of the measurement region. In the case of Part (b) of FIG. 4-2, the measurement region 411 is set to have a circular shape, and the boundary 412 is set to have a regular polygonal shape surrounding the measurement region 411. In the case where the measurement region 411 has such a shape not rectangular, the cell 413 is preferably set to have a triangle shape. When the basic shape of the cell 413 is set to be triangular, the cells can be arranged within the measurement region 411 without overlapping or leaving gaps. In the case of FIG. 4-2, the physical property value 42 is represented on a scale of four levels.

FIG. 5 illustrates examples of output displays by the physical property value-display quantity conversion part 53. Parts (a) and (b) of FIG. 5 correspond to part (c) of FIG. 4-1. The measurement object is also a living body, here. If the equation of motion evaluated by using the evaluation quantity is an elastodynamic equation, the physical property values are the Lamé's constant $\lambda$, the Lamé's constant $\mu$, the density of inertia $\rho$, and the attenuation coefficient c. The possible display quantity is any of $\lambda$, $\mu$, $\rho$, c, and functions thereof such as a bulk modulus, a longitudinal wave velocity, a transverse wave velocity, a Poisson's ratio, a Young's modulus, and an impedance. The display 7 may display one or more (preferably plural) ones of these display quantities at the same time on the same screen. Here, part (a) of FIG. 5 is a display example of the longitudinal wave velocity while part (b) of FIG. 5 is a display example of the attenuation coefficient. It is preferable to display these two pictures, for example, on the screen of the display 7 at the same time. The display of plural display quantities on the same screen enables easy recognition of information useful to diagnose a tumor or the like, which is a portion having the impedance (shape) same as, but a bulk modulus (hardness) different from those of other portions.

(Example of Data Format)

Figure 12:
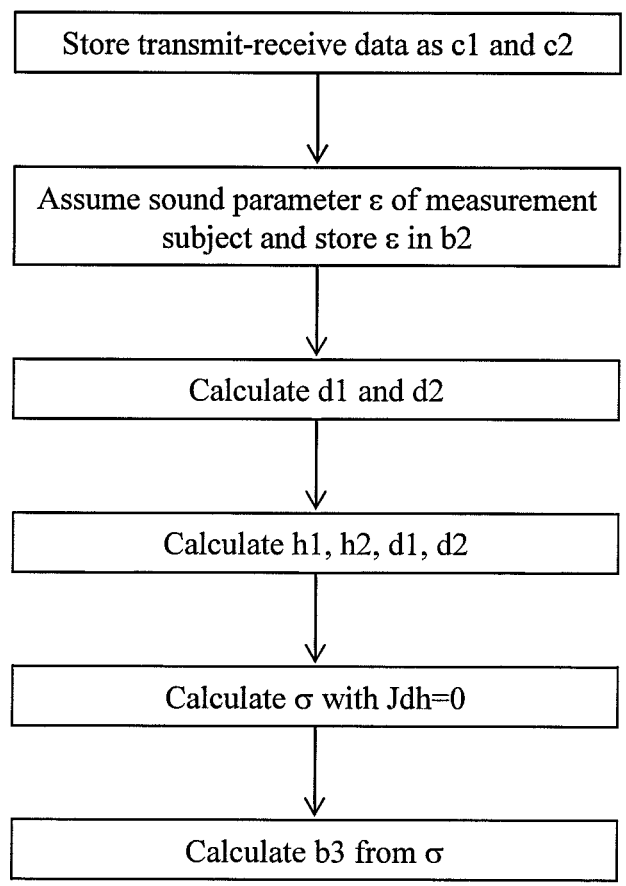
FIG. 12 is a detailed diagram of a data processing flow.

FIG. 6 illustrates one example of data formats. The data formats illustrated in FIG. 6 are similar to the formats described in a general textbook for the finite element method. FIG. 12 illustrates details of a processing flow in the case of using the data in FIG. 6. Part (a) of FIG. 6 illustrates small cells into which an imaging subject region is virtually divided as illustrated in part (b) of FIG. 4-1. The cells are assigned numbers as illustrated in part (a1) of FIG. 6, and the sides of the cells are also assigned numbers as illustrated in part (a2) of FIG. 6. This example indicates an example in which the number of cells is 9 and the number of sides is 24. The sides depicted by a double line in part (a2) of FIG. 6 are the boundary of the imaging region, where actual transmit-receive data (sound pressure value, a sound pressure spatial gradient) is available; these values are unknown on the sides indicated by a single line. The physical property value is set to be defined for each cell, and the measurement value is set to be defined for each side.

Under these settings, the physical property value $\epsilon_{Ai}$ is calculated by using the data formats (b) to (e) in FIG. 6 in the physical property value calculation step S200. The data (b1) is a true value $\epsilon_A$ of the physical property value, the data (b2) is an assumed value $\epsilon_i$ of the physical property value, and the data (b3) is a difference value $d\epsilon$ between an i-th assumed value and an i+1-th assumed value, each of which is expressed as a vector in a size of 9 (the number of cells). The data (c1) is a sound pressure value p (Dirichlet condition) of each side, and the data (c2) is a sound pressure gradient value $kd_np$ (Neumann condition) of each side. Both of (c1) and (c2) are vectors in a size of 24 (the number of sides), and take values only on the sides on the boundary, indicated by the double line in part (a2) of FIG. 6, in other words, the sides where the actual transmit-receive data is acquired (the 1st, 3rd, 6th, 8th, 9th, 11th, 16th, 18th, 20th, 22nd, 23rd, 24th sides in this example), while having a value of 0 on the other sides.

The data (d1) is a matrix GD[i][j] expressing a Green's function of the equation of motion for the Dirichlet condition, whereas the data (d2) is a matrix GN[i][j] expressing a Green's function of the equation of motion for the Neumann condition. Both of (d1) and (d2) have a size of 24 (the number of sides) rows and 24 columns, and are functions of the set value of the physical property value. In other words, if the assumed value of the physical property value is changed, the values of the matrices are changed. Please see a general text book for relations between the physical property value and the matrices. By using these data, the physical property value described with reference to FIG. 2-1 and FIG. 2-2 is configured. The following description is provided for an example using the non-uniformity detection equation residual quantity. Specifically, firstly, the sound pressure and the sound pressure spatial gradient of the transmit-receive data on the boundary of the observation object are stored in (c1) and (c2), respectively. Next, the assumed value (b2) of the physical property value is set, and the (d1) matrix GN[i][j], and (d2) matrix GN[i][j] are calculated. Subsequently, when g denotes a diagonal matrix in which the sides on the boundary take 1 while the other sides take 0, Ng denotes a matrix obtained by subtracting g from an identity matrix, and $\sigma$ denotes a virtual vector in which the non-uniformity of the physical property value is converted into an external force, the solution h1 under the Dirichlet condition (the boundary value=actual transmit-receive data) is expressed as $GD^{-1}*(p+Ng*p*g)$, the solution d1 under the Dirichlet condition (the boundary value=0; the non-uniformity is taken into account) is expressed as $GD^{-1}*(\sigma)$, the solution h2 under the Neumann condition (the boundary value=0; the non-uniformity is taken into account) is expressed as $GN^{-1}*(kd_np)$, the solution d2 under the Neumann condition (the boundary value=0; and the non-uniformity is taken into account) is expressed as $GN^{-1}*(\sigma)$. Thus, the non-uniformity detection equation residual quantity of $J_{dh}=(-h1+h2)-(d1-d2)$ is calculated from $-GD^{-1}*(p+Ng*p*g)+GN^{-1}*(kd_np)-(GD^{-1}-GN^{-1})*(\sigma)$.

In this calculation, a value of $\sigma$ is calculated with $J_{dh}=0$, the deviation quantity $d\epsilon_i$ of the physical property value is calculated by using the relation expressed by (2) Equation (i.e., $GN(d\epsilon_i)*(h1+d1)=\sigma$), and the set value $\epsilon_i$ of the physical property value is updated to $\epsilon_{i+1}=\epsilon_i+d\epsilon_i$.

The transmit-receive wave data c1 and c2 in FIG. 6 represents data at a certain frequency component obtained as a result of frequency analysis on time series data. From a result of analysis for each level of frequency, the distributions of physical property value for the respective frequency components may be displayed, or instead, the distribution of physical property value obtained by adding up the physical property values at the respective frequency components within a band available for transmission and reception may be displayed. Moreover, the idea of the present invention naturally includes modifying the foregoing equations appropriately to be suitable to time series data, and displaying a transient physical property value distribution.

(Relationship Between Evaluation Quantity and how to Calculate Physical Property Value)

FIG. 7 illustrates conceptual diagrams each for explaining a relationship between an evaluation quantity and how to calculate a physical property value. In FIG. 7, part (a1) illustrates a case where the equation residual quantity $J_{eq}$ is used as the evaluation quantity and the physical property value that makes the evaluation quantity be 0 is outputted as a true value from S200; part (a2) illustrates a case where the equation residual quantity $J_{eq}$ is used as the evaluation quantity and the physical property value that maximizes the evaluation quantity is outputted as a true value from S200; part (b) illustrates a case where the non-uniformity detection equation residual quantity $J_{hd}$ is used as the evaluation quantity and the physical property value that maximizes the evaluation quantity is outputted as a true value; and part (c) illustrates a case where a product of the equation residual quantity $J_{eq}$ and the conditional equation residual quantity $J_c$ is used as the evaluation quantity and the physical property value that maximizes the evaluation quantity is outputted as a true value. In the cases (a1) and (a2) where the equation residual quantity $J_{eq}$ is used as the evaluation quantity, the set value $\epsilon_1$ (i=1, 2, . . . ) of the physical property value $\epsilon$ is updated by sampling in a conventional method, and thereby the true value of the physical property value converges on $\epsilon_A$. In the conventional sampling method, the next set value $d\epsilon_{i+1} = \epsilon_i + d\epsilon_i$ is determined by updating $\epsilon$ randomly or by using a difference $d\epsilon_i = c^* dJ/d\epsilon$ ($\epsilon = \epsilon_i$) proportional to a local slope $dJ/d\epsilon$ at the current set value $\epsilon_i$ of the evaluation quantity. In the case (b) where the non-uniformity detection equation residual quantity $J_{hd}$ is used as the evaluation quantity, the next set value $d\epsilon_{i+1} = \epsilon_i + d\epsilon_i$ is determined by calculating a difference between an estimated value $\epsilon_A$ of the true value and the current set value. The method (b) of updating the physical property value by estimating a difference (deviation quantity) between the true value and the set value is able to converge the set value on the true value more quickly than the method (a) that uses only information on the set value without using information on the true value. In the case (c) where the product of the equation residual quantity $J_{eq}$ and the conditional equation residual quantity $J_c$ is used as the evaluation quantity, the conditional equation thus given excludes physical property values not satisfying the conditional expression from an evaluation range, and thereby narrows down the evaluation range as indicated by a curve line having a smaller width than in parts (a2) and (b) in FIG. 7. Thus, in this case, the value is prevented from converging on a physically-inappropriate solution even when there is a shortage of measurement values, and the convergence on the true value can be achieved more quickly than in part (a2) of FIG. 7.

(Example of Transmit Sequence Transmission)

FIG. 8 illustrates one example of a basic sequence of a transmit sequence outputted by the transmit-receive data acquisition part 51. In this embodiment, the transceiver elements 21 transmit and receive the transmit sequence two or more times. Part (a) of FIG. 8 is an example of first transmission-and-reception, and part (b) of FIG. 8 is an example of second transmission-and-reception. In the drawing, "21" indicates transmission elements that outputs the transmit sequence, "22" indicates transmission waveforms, and "23" indicates wave vectors. In this example, multiple transceiver elements 21 transmit signals having an equal burst length at the same time in each of the first and second transmit sequences. In this way, a plane burst wave 22 having phase planes aligned with each other is generated.

In the case of FIG. 8, the carrier frequency is changed between the first transmit sequence and the second transmit sequence. The carrier frequency is preferably variable within a range of 0.5 MHz, inclusive, to 10 MHz. In addition, the spatial layout of the transceiver elements 21 is set to have spacing inversely proportional to the carrier frequency. Moreover, the directivities are synthesized so that the corresponding wave vectors 23 can have the same form in the first and second transmit sequences. To be more specific, the directivities are synthesized so that a main lobe 23LM and grating lobes 23LG1, 23LG2 of the first transmitted wave at a low carrier frequency are directed at the same angles, respectively, as a main lobe 23HM and grating lobes 23HG1, 23HG2 of the second transmitted wave at a high carrier frequency.

Note that 21L1 (indicated by hatching) in part (a) of FIG. 8 indicates the center of mass in the element layout, and the number of transceiver elements 21 used for the first transmitted wave and the number of transceiver elements 21 used for the second transmitted wave do not have to be equal to each other. If the carrier frequency in the first transmission and the carrier frequency in the second transmission have a difference of two times, a subarray including two transceiver elements 21 may be placed at each position of the center of mass in the first transmission.

Employment of the basic sequence having the aforementioned transmission waveforms and spatial layout of the transceiver elements 21 enable generation of sound fields which have simple and similar forms only having a difference between their carrier frequencies. This results in an improvement of the identification accuracy of the sound speed that is a ratio between the Lamé's constants and the density of inertia by using the evaluation quantity. Moreover, identification accuracy of inertia mass can be improved by use of a difference between the carrier frequencies. In addition, use of plane burst waves as in this example can improve S/N due to measurement noise, as compared with a case where only one transceiver element 21 transmits a signal.

Figure 10:
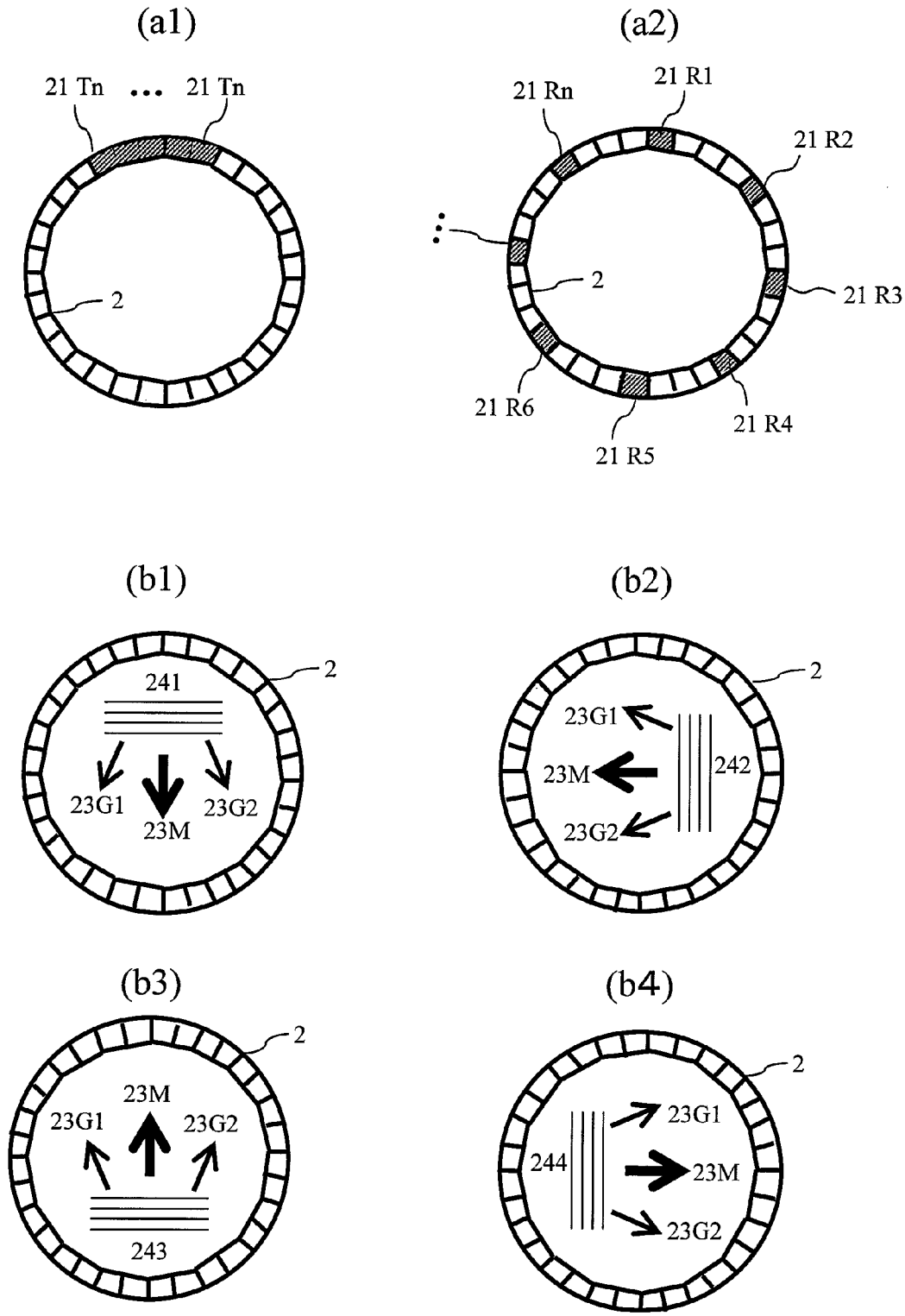
FIG. 10 illustrates conceptual diagrams of one example of a transmit sequence outputted by the transmit-receive data acquisition part of the image reconstruction device according to the embodiment.

FIG. 9 and FIG. 10 illustrate output examples of transmit sequences by the transmit-receive data acquisition part 51. zy7 illustrates a case where the probe 2 is in contact with part of the boundary of a measurement object 0, and FIG. 9 illustrates a case where the probe 2 is in contact with the entire boundary of the measurement object 0.

Parts (a1) and (a2) of FIG. 9 illustrate layout examples of transmitter elements T and receiver elements R, respectively. The layout of the transmitter elements T is sparse to the extent causing no problem in generation of grating, and is dense to the extent capable of forming a plane wave. On the other hand, the spatial layout of the receiver elements R is a layout that maximizes the angle of view in the measurement region. As a result of employing, as the spatial layout of the receiver elements R, the layout that maximizes the angle of view in the measurement region, the calculation accuracy of the physical property value is improved.

Parts (b1) to (b3) of FIG. 9 illustrate a wave transmit sequence in which the basic sequence explained in reference to FIG. 8 is repeated multiple times so that wave vectors inside a measurement region traverse in different directions to the extent possible. As a result of employing, as the spatial layout of the receiver elements R, the layout that maximizes the angle of view in the measurement region, information on as many independent components as possible within the constraints on the device configuration can be acquired in the eigenspace of the matrix included in the evaluation quantity, which leads to improvement in coefficient identification accuracy in a case of a shortage of measurement points.

In the case where the probe 2 is in contact with part of the boundary of the measurement object 0 as illustrated in FIG. 9, the directions of the wave vectors can be changed as needed in such a way that the layout positions of the transmitter elements T are fixed and that a phase difference is provided to time points at which the respective transmitter elements T transmit signals.

On the other hand, in the case where the probe 2 is in contact with the entire boundary of the measurement object 0 as illustrated in FIG. 10, the directions of the wave vectors can be changed by changing the layout positions of the transmitter elements T.

For instance, the example in FIG. 9 indicates an example in which six times of transmissions-and-receptions are performed in the case where the probe 2 is in contact with the part of the boundary of the measurement object 0. The inter-element spacing for placing the transmitter elements T used for the even-numbered transmissions-and-receptions is dense to some extent as illustrated in part (a1) of FIG. 9. On the other hand, the inter-element spacing for placing the transmitter elements T used for the odd-numbered transmissions-and-receptions is set to be twice wider than the inter-element spacing for the even-numbered transmissions-and-receptions. The receiver elements R are fixed throughout the first to 6th transmissions-and-receptions as illustrated in part (a2) of FIG. 9.

A low-frequency burst plane wave is transmitted in the directions in part (b1) of FIG. 9 in the first transmission-and-reception, a high-frequency burst plane wave is transmitted in the directions in part (b1) of FIG. 9 in the second transmission-and-reception, a low-frequency burst plane wave is transmitted in the directions in part (b2) of FIG. 9 in the third transmission-and-reception, a high-frequency burst plane wave is transmitted in the directions in part (b2) of FIG. 9 in the fourth transmission-and-reception, a low-frequency burst plane wave is transmitted in the directions in part (b3) of FIG. 9 in the fifth transmission-and-reception, and a high-frequency burst plane wave is transmitted in the directions in part (b3) of FIG. 9 in the 6th transmission-and-reception. As a matter of course, the receive elements R receive the receive waves corresponding to the respective burst plane waves. Then, the evaluation quantities are formed by giving these six equations of motion as a system of equations.

The example in FIG. 10 indicates an example in which 8 times of transmissions-and-receptions are performed in the case where the probe 2 is in contact with the entire boundary of the measurement object 0. The transmitter elements T used for the even-numbered transmissions-and-receptions are placed within a localized range and with inter-element spacing dense to some extent. On the other hand, the inter-element spacing for placing the transmitter elements T used for the odd-numbered transmissions-and-receptions is set to be twice wider than the inter-element spacing for the even-numbered transmissions-and-receptions. The receiver elements R are placed evenly and fixedly throughout the first to 8th transmissions-and-receptions as illustrated in part (a2) of FIG. 10.

The transmitter elements T placed on the upper side in the drawing with inter-element spacing of 2d transmit a low-frequency burst plane wave in the directions in part (b1) of FIG. 10 in the first transmission-and-reception, the transmitter elements T placed on the upper side in the drawing with inter-element spacing of d transmit a high-frequency burst plane wave in the directions in part (b1) of FIG. 10 in the second transmission-and-reception, the transmitter elements T placed on the right side in the drawing with inter-element spacing of 2d transmit a low-frequency burst plane wave in the directions in part (b2) of FIG. 10 in the third transmission-and-reception, the transmitter elements T placed on the right side in the drawing with inter-element spacing of d transmit a high-frequency burst plane wave in the directions in part (b2) of FIG. 10 in the fourth transmission-and-reception, the transmitter elements T placed on the lower side in the drawing with inter-element spacing of 2d transmit a low-frequency burst plane wave in the directions in part (b3) of FIG. 10 in the fifth transmission-and-reception, the transmitter elements T placed on the lower side in the drawing with inter-element spacing of d transmit a high-frequency burst plane wave in the directions in part (b3) of FIG. 10 in the 6th transmission-and-reception, the transmitter elements T placed on the left side in the drawing with inter-element spacing of 2d transmit a low-frequency burst plane wave in the directions in part (b4) of FIG. 10 in the 7th transmission-and-reception, and the transmitter elements T placed on the left side in the drawing with inter-element spacing of d transmit a high-frequency burst plane wave in the directions in part (b4) of FIG. 10 in the 8th transmission-and-reception. As a matter of course, the receive elements R receive the receive waves corresponding to the respective burst plane waves. Then, the evaluation quantities are formed by giving these eight equations of motion as a system of equations.

Figure 11:
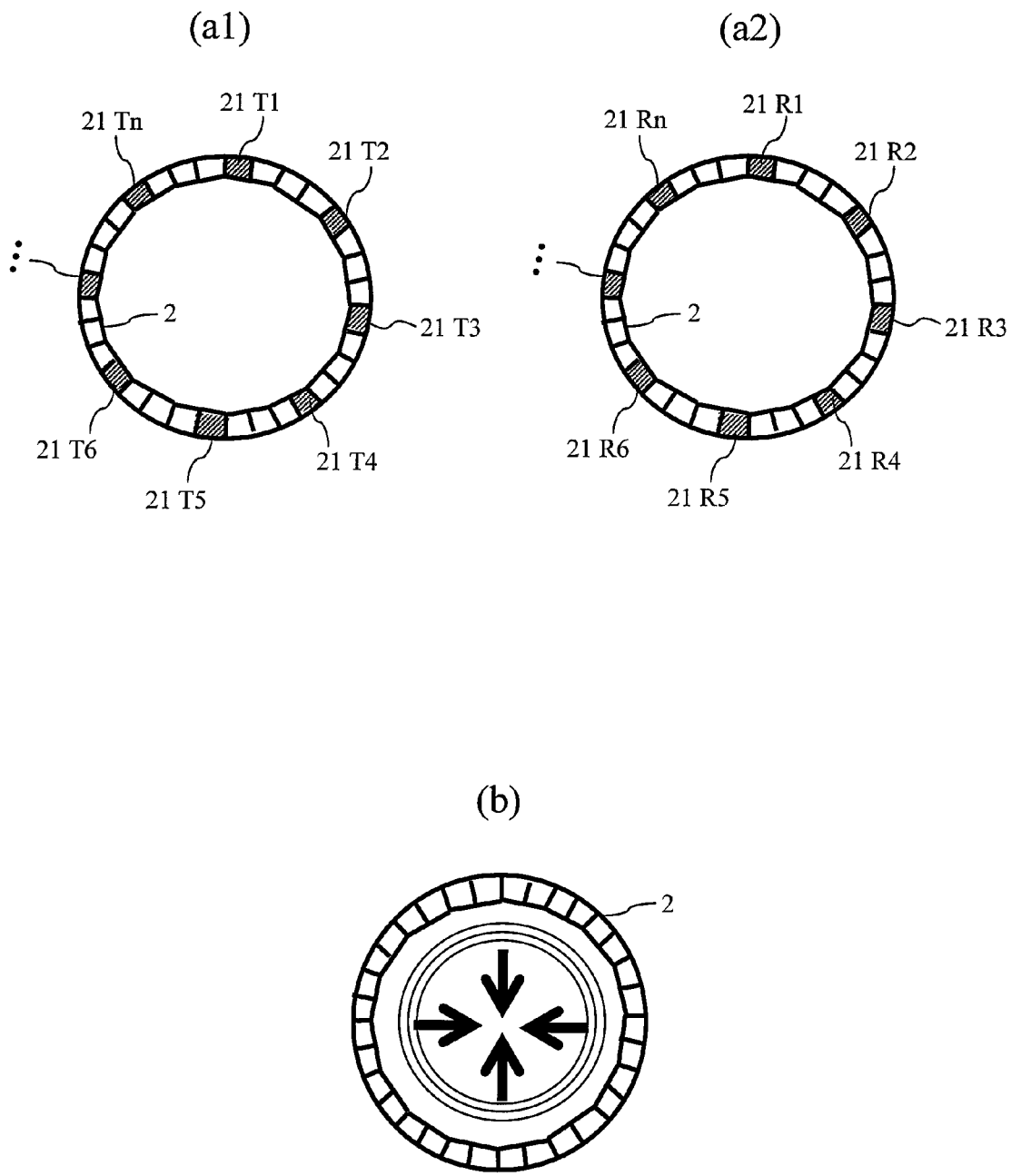
FIG. 11 illustrates conceptual diagrams of another example of a transmit sequence outputted by the transmit-receive data acquisition part of the image reconstruction device according to the embodiment.

FIG. 11 illustrates another example of the transmit sequence outputted by the transmit-receive data acquisition part 51. In the cases in FIG. 9 and FIG. 10, the layout of the transmitter elements T is changed for each transmission-and-reception to direct the transmission directions of the burst plane wave in one particular direction. However, in a case where the transmit-receive sequence is set based on a standard in which the sound field formed in the measurement region is symmetrical, a cylindrical wave may be generated as illustrated in part (b) of FIG. 11, if the transceiver elements 21 can be placed along a circumference as illustrated in parts (a1) and (a2) of FIG. 11.

In this case, the same transceiver elements 21 placed on the circumference at equal intervals as illustrated in parts (a1) and (a2) of FIG. 11 may be each used as the transmitter element T and the receiver element R by switching. In this case, the transceiver elements 21 are used without being switched between the transmitter elements T and the receiver elements R, and thus the same elements can be used for both of transmission and reception. This prevents noise inclusion from a switch for switching the elements, and leads to improvement of calculation accuracy of a physical property value.

The description has been provided for the examples in which the transmit-receive data is transmitted and received 6 times in FIG. 9, whereas the transmit-receive data is transmitted and received 8 times in FIG. 10. However, the evaluation quantity J is expressed by a matrix of N rows and N columns, and has a basis number of N, where N=(the number of elements)*(transmission-and-reception time period)/(time sampling interval). For this reason, the transmit-receive data of N times of transmissions-and-receptions and the transmit-receive data of N or more times of transmissions-and-receptions have the same information quantity. In the meantime, imaging apparatuses are required to capture an image within a short period of time. What should be done to attain both of satisfactory accuracy of a reconstructed image and imaging period is to avoid an N+1-th or following transmission-and-reception that does not increase an information quantity directly affecting the accuracy of the image but elongates the imaging period. The number of transmissions-and-receptions is preferably equal to or smaller than N=(the number of elements)*(transmission-and-reception time period)/(time sampling interval).

EXPLANATION OF REFERENCE NUMERALS

1: probe
2: main body
3: transmitter
4: receiver
5: signal processor
51: transmit-receive data acquisition part
52: physical property value calculation part
53: physical property value-display quantity conversion part
6: memory
7: display
8: input means
9: controller

The invention claimed is:

1. An image reconstruction method of transmitting and receiving signals to and from a measurement region and determining a quantity of a physical property of the measurement region through numerical calculation using a measuring apparatus, the method comprising:
a transmit-receive data acquisition step, by a transmit-receive data acquisition part of the measuring apparatus, of transmitting and receiving signals to and from the measurement region;
a physical property value calculation step, by a physical property value calculation part of the measuring apparatus, of calculating a physical property value from an actual receive signal received from the measurement region; and
a physical property value-display value conversion step, by a physical property value-display value conversion part of the measuring apparatus, of converting the physical property value into a display value, wherein
the physical property value calculation step includes a step of calculating, by a processor in communication with the transmit-receive data acquisition part, the physical property value calculation part, and the physical property value-display value conversion part, an estimate of a deviation quantity of an assumed physical property value, the estimate derived from the transmit-receive data acquired in the transmit-receive data, a distribution of the assumed physical property value, and an equation formed in consideration of and a wave propagation,
the deviation quantity of the physical property value is calculated, by the processor, as an evaluation quantity J which is any one of, a linear sum of any two or more of, a product of any two or more of, or an exponential function including as an exponent any one of:
an equation residual quantity that is a residual being a difference between an operator term and an external force term of an equation of motion,
a non-uniformity detection equation residual quantity that is a residual of an equation of detecting non-uniformity of the physical property value according to the matching degree between solutions of the equation of motion under two types of boundary conditions, and
a conditional equation residual quantity that is a residual of a constraint condition; and
a sum of the assumed physical property value and the deviation quantity is outputted, by the processor, as a calculated physical property value.

2. The image reconstruction method according to claim 1, wherein
the physical property value calculation step determines whether the evaluation quantity J that is derived from the equation and takes 0 or an extremum when the physical property value is a true value BA fulfills a convergence condition for a set value of the physical property value; if the evaluation quantity J does not fulfill the convergence condition, updating the set value of the physical property value through update of an estimated value of the deviation quantity dB of the set value of the physical property value from the true value BA and then making the determination again; and if the evaluation quantity J fulfills the convergence condition, outputting the physical property value after the update as a calculation result.

3. The image reconstruction method according to claim 1, wherein
the step of estimating the deviation quantity from the equation formed m consideration of the wave propagation divides the measurement region into small spatial cells and calculates the deviation quantity of each of the cells.

4. The image reconstruction method according to claim 2, wherein
the physical property value calculation step includes:
a deviation quantity estimation step of estimating a deviation quantity $d\epsilon i$ that is a difference between an i-th set value $\epsilon i$ of the physical property value and the true value $\epsilon A$, where i is an integer of 1 to n−1 (n is an integer of 2 or larger and is a maximum value of the number of times of setting the physical property value $\epsilon i$);
a physical property value update step of giving $\epsilon i + d\epsilon i$ as an n+1-th set value $\epsilon i+1$ of the physical property value, where $\epsilon i$ is an i-th set value of the physical property value and $d\epsilon i$ is an estimated deviation quantity;
a convergence determination step of determining that the physical property value $\epsilon i$ is converged on the true value $\epsilon i$ when the evaluation quantity J having the physical property value $\epsilon i$ as a variable fulfills $|J(\epsilon i)|<e$ or $|J(\epsilon i+1)-J(\epsilon i)|<e$ where e is a preset minute quantity.

5. The image reconstruction method according to claim 4, wherein
a transmit-receive sequence is a transmit-receive sequence making a large contribution to the estimation of the deviation quantity $d\epsilon j$.

6. The image reconstruction method according to claim 2, wherein
the transmit-receive data acquisition step includes a transmit-receive sequence determination step of determining the number of times of performing transmissions-and-receptions by transceiver elements, a spatial layout of the transceiver elements and transmit-and-receive waveforms, and obtaining results of the transmissions-and-receptions, and
the transmit-receive sequence determination step outputs a transmit-receive sequence in which:

the number of times of performing transmissions-and-receptions by the transceiver elements is two or more, the transmit waveform at least includes a plurality of plane burst waves having an equal burst length but having different carrier frequencies within a range of 0.5 MHz to 10 MHz, both inclusive, the spatial layout of the transmitter elements has spacing inversely proportional to the carrier frequencies, and a spatial layout of receiver elements is a layout that maximizes an angle of view in the measurement region.

7. The image reconstruction method according to claim 6, wherein the transmit-receive sequence determination step outputs a transmit-receive sequence in which:

the number of times of performing transmissions-and-receptions by the transceiver elements is two or more, and the frequency used in the transmission-and-reception becomes lower as a transmission-and-reception time becomes earlier.

8. The image reconstruction method according to claim 1, wherein the physical property value calculation step outputs the physical property value that makes a quantity of a linear sum or a product of exponential function be an extremum, where the linear sum includes as one term, or the product of exponential function includes as one factor, the non-uniformity detection equation residual quantity given by a residual being a difference between:

a differential vector that is a difference between a solution under a Neumann boundary condition and a solution under a Dirichlet boundary condition in a case where a boundary value is actual transmit-receive data, and a product of a vector expressing the non-uniformity of the physical property value and an operator matrix that is a difference between a Green's function of the equation of motion under a Neumann boundary condition and a Green's function of the equation of motion under a Dirichlet boundary condition in a case where the boundary value is zero.

9. The image reconstruction method according to claim 2, wherein the physical property value calculation step outputs the physical property value that makes a quantity of a linear sum or a product of exponential function be an extremum, where the linear sum includes as one term, or the product of exponential function includes as one factor, a conditional equation residual quantity of the evaluation quantity that includes at least one of a prior probability term that is a prior probability expressing the nature of a distribution of the evaluation quantity of the physical property value, and a low order approximation matching quantity indicating a matching degree with an image reconstructed by a method of synthesizing directivities or projection mapping.

10. The image reconstruction method according to claim 2, wherein the physical property value calculation step calculates the physical property value that makes the evaluation quantity be an extremum, by using metropolis sampling that is one of stochastic methods.

11. The image reconstruction method according to claim 1, wherein the equation residual quantity is a residual of any equation among a frequency representation of an elastodynamic equation, a time response representation of the elastodynamic equation and a Helmholtz potential representation of the elastodynamic equation, the physical property value is one or more of a Lamé's constant $\lambda$, a Lamé's constant $\mu$, a density of inertia p, an attenuation coefficient c, a ratio between any of the Lamé's constants and the density of inertia, a ratio between any of the Lamé's constants and the attenuation coefficient, and an external force f, and the display quantity is any one or more of the $\lambda$, the $\mu$, the p, the c, and functions thereof including a bulk modulus, a longitudinal wave velocity, a transverse wave velocity, a Poisson's ratio, and a Young's modulus, an impedance, and the external force.

12. A measuring apparatus for transmitting and receiving signals to and from a measurement region and determining a quantity of a physical property of the measurement region through numerical calculation, the apparatus comprising:

a transmit-receive data acquisition part configured to transmit and receive signals to and from the measurement region;

a physical property value calculation part configured to calculate a physical property value from an actual receive signal received from the measurement region; and a physical property value-display value conversion part configured to convert the physical property value into a display value, wherein the physical property value calculation part includes a processor configured to calculate an estimate of a deviation quantity of an assumed physical property value, the estimate derived from the transmit-receive data acquired in the transmit-receive data, a distribution of the assumed physical property value, and an equation formed in consideration of a wave propagation, the processor is further configured to calculate the deviation quantity of the physical property value is calculated as an evaluation quantity J which is any one of, a linear sum of any two or more of, a product of any two or more of, or an exponential function including as an exponent any one of:

an equation residual quantity that is a residual being a difference between an operator term and an external force term of an equation of motion, a non-uniformity detection equation residual quantity that is a residual of an equation of detecting non-uniformity of the physical property value according to the matching degree between solutions of the equation of motion under two types of boundary conditions, and a conditional equation residual quantity that is a residual of a constraint condition; and the processor is further configured to output a sum of the assumed physical property value and the deviation quantity as a calculated physical property value.

* * * * *